United States Patent
Borgonovo

(10) Patent No.: US 11,517,179 B1
(45) Date of Patent: *Dec. 6, 2022

(54) FOOTWEAR CLEANING SYSTEM

(71) Applicant: Cecilia Borgonovo, St. Petersburg, FL (US)

(72) Inventor: Cecilia Borgonovo, St. Petersburg, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/652,329

(22) Filed: Feb. 24, 2022

Related U.S. Application Data

(63) Continuation of application No. 17/453,071, filed on Nov. 1, 2021, now Pat. No. 11,291,349.

(60) Provisional application No. 63/108,519, filed on Nov. 2, 2020.

(51) Int. Cl.
| | |
|---|---|
| *A47L 23/02* | (2006.01) |
| *A46B 13/00* | (2006.01) |
| *A46B 13/02* | (2006.01) |
| *A46B 9/00* | (2006.01) |
| *A61L 2/10* | (2006.01) |

(52) U.S. Cl.
CPC .............. *A47L 23/02* (2013.01); *A46B 9/005* (2013.01); *A46B 13/008* (2013.01); *A46B 13/02* (2013.01); *A61L 2/10* (2013.01); *A46B 2200/306* (2013.01); *A61L 2202/11* (2013.01); *A61L 2202/122* (2013.01); *A61L 2202/17* (2013.01)

(58) Field of Classification Search
CPC ............ A46B 13/008; A46B 2200/306; A47L 9/0472; A47L 11/16; A47L 11/162; A47L 11/2025; A47L 11/206; A47L 11/2065; A47L 11/283; A47L 11/293; A47L 11/305; A47L 11/4038; A47L 23/00; A47L 23/02
USPC .............................................. 15/34, 36, 97.2
See application file for complete search history.

(56) References Cited

U.S. PATENT DOCUMENTS

| | | | | |
|---|---|---|---|---|
| 4,998,314 | A * | 3/1991 | Borofsky | ............ A47L 11/4036 15/49.1 |
| 2003/0051300 | A1 * | 3/2003 | Ferrari | .................... A47L 23/02 15/310 |

\* cited by examiner

*Primary Examiner* — Michael D Jennings
*Assistant Examiner* — Aaron R McConnell
(74) *Attorney, Agent, or Firm* — Owen G. Behrens; Paul Murty; Smith & Hopen, P.A.

(57) ABSTRACT

A footwear cleaning system including an outer housing that encases an internal compartment, which is designed, sized, and shaped to receive a footwear item therein, such as an athletic shoe, dress shoe, platform shoe, or other similar footwear item. The footwear cleaning system includes one or more rotatable cleaning disks disposed within the internal compartment, such that the cleaning disks are configured to interact with a bottom surface of a footwear item. One or more fluidic conduits terminate at a location that is proximate to the internal compartment, such that water, cleaning solutions, concentrated cleaning products, alcohol, and other fluids can be dispelled into the internal compartment to interact with a footwear item.

19 Claims, 19 Drawing Sheets

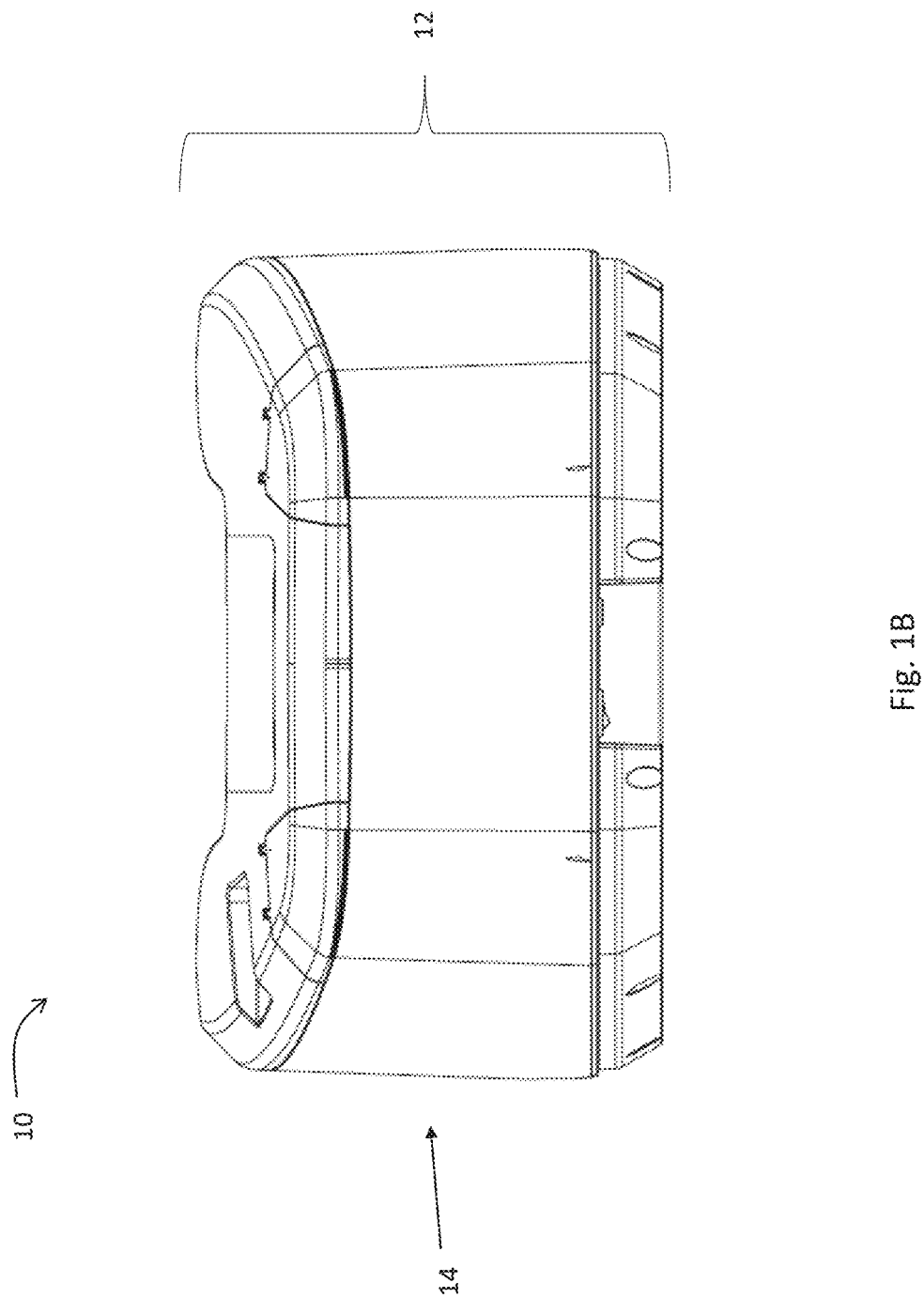

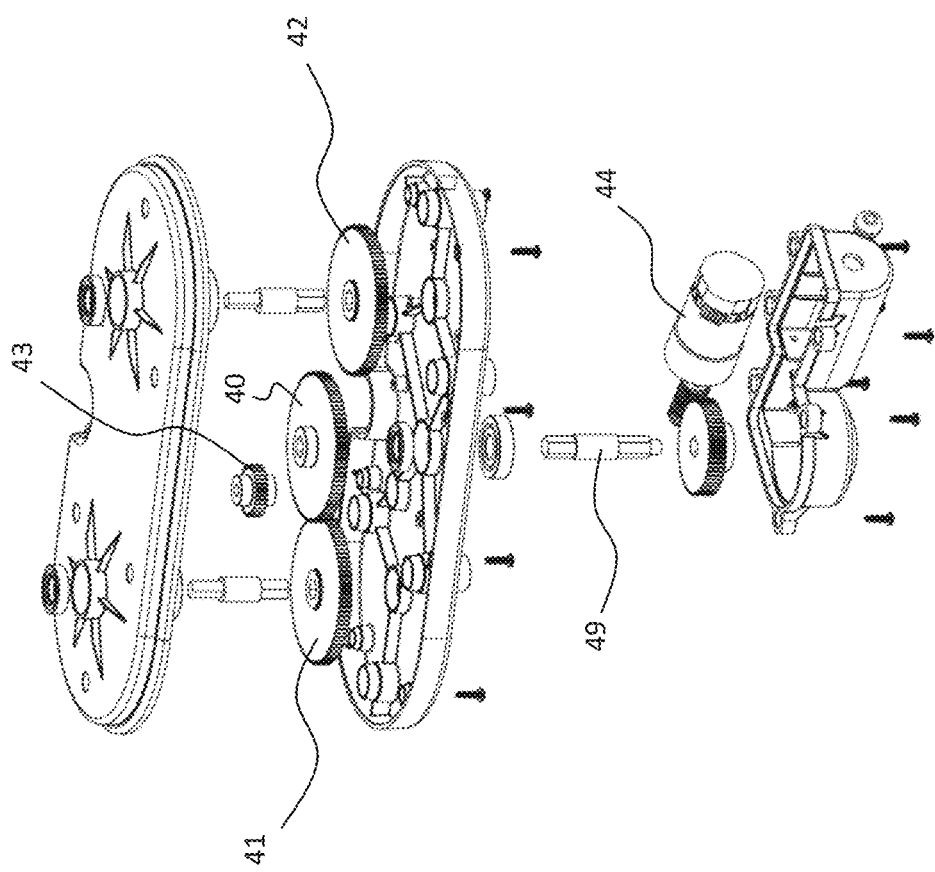

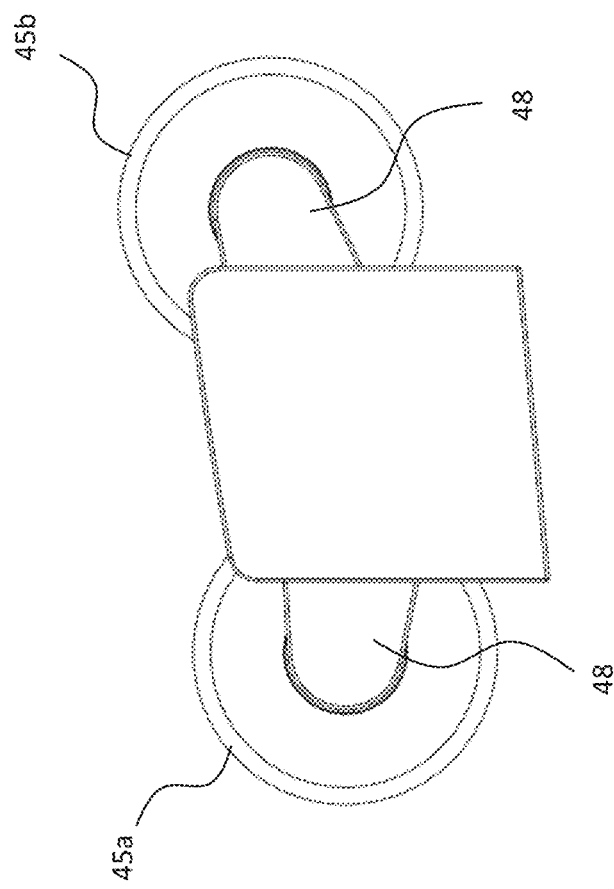

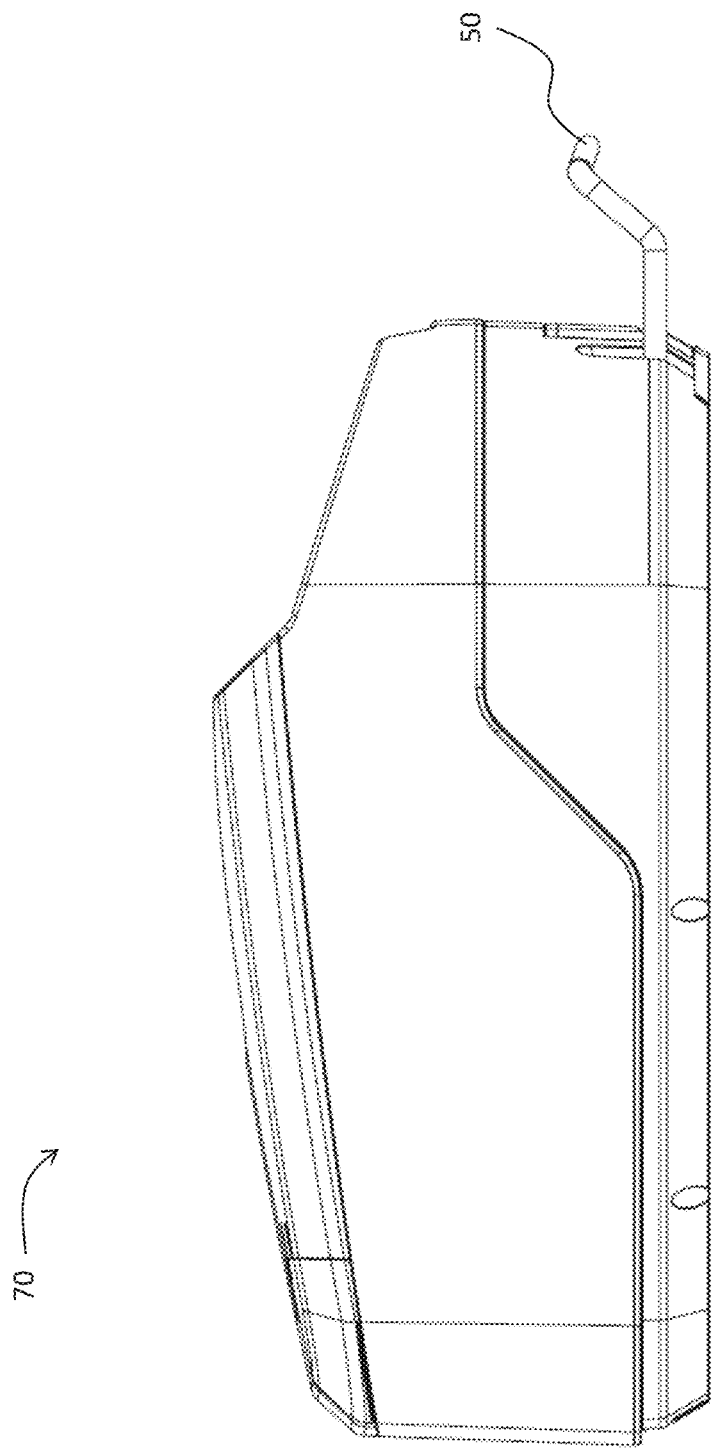

FOOTWEAR CLEANING SYSTEM

CROSS-REFERENCE TO RELATED APPLICATIONS

This nonprovisional application is a continuation of and claims priority to nonprovisional application Ser. No. 17/453,071, entitled "Footwear cleaning system," filed on Nov. 1, 2021, which claims the benefit of provisional application No. 63/108,519, entitled "Shoe cleaner," filed on Nov. 2, 2020, by the same inventor, the entireties of which are incorporated herein by reference.

BACKGROUND OF THE INVENTION

1. Field of the Invention

This invention relates, generally, to cleaning systems. More specifically, it relates to a cleaning system for footwear, such as shoes, including rotatable cleaning pads having alternating bristle sections to remove dirt, debris, bacteria, and other contaminants from the footwear.

2. Brief Description of the Prior Art

In modern societies around the world, humans often wear one or more items of footwear when located outside of a residential home. For example, people typically wear exercise shoes when engaging in physical activities outside, such as walking, running, playing sports, and other similar physical activities. Similarly, people attending a gathering, such as a business conference or a celebration, tend to wear footwear to the event. Often, individuals put on a pair of shoes prior to leaving a residential home, and remove the pair of shoes after arriving back at the residential home.

Once applied, individuals typically wear the pair of shoes throughout the day spent outside of the residential home. As a result of transportation along ground surfaces, whether simply walking or utilizing transportation vehicles to travel between locations or engaging in a physical activity, the footwear worn by an individual forms a barrier between the individual's feet and the ground surface. Since many ground surfaces outside of the individual's residence are public pathways or other commonly-tread areas, there is a high risk of the sole of the footwear coming into contact with one or more contaminants.

For example, exterior ground surfaces, such as concrete sidewalks, can contain bacteria, harmful chemicals, aerosolized virus particles, and other contaminants that can at least temporarily attach to the sole of footwear items. When an individual interacts with the ground surface, such as by walking on the surface via footwear, the footwear can become contaminated with substances that are disposed on the ground surface. Particularly during the global severe acute respiratory syndrome coronavirus 2 (SARS-CoV-2) pandemic, reductions of potential contaminant spread gained new importance in daily lives across the world.

When arriving to a residential home or other establishment within which an individual plans to spend an extended amount of time, the individual may continue wearing footwear or may remove footwear. However, the individual may not wish to remove his or her footwear for a variety of reasons, which could result in the individual introducing contaminants from the footwear to the establishment. In some cultures, the wearing of footwear indoors is discouraged, and it is customary to remove shoes prior to entering a home to prevent the spread of contaminants. However, the removal of shoes prior to entering a home is not universal, and many individuals continue to wear shoes throughout a visit to a home. The result is that contaminants can spread throughout the home, particularly when an unclean item of footwear interacts with a carpet or other fabric within the home, since the contaminants can be permanently retained by the carpet or other fabric.

While attempts have been made to provide shoe cleaners that are designed to clean the soles of shoes and/or the top and side exterior surfaces of the shoes, such devices are typically manual in nature. For example, brushes exist to remove blemishes and reduce contaminants on shoes, which typically require manual labor to clean the shoes. To date, effective automated or powered shoe cleaners do not exist that effectively and efficiently wash, scrub, and sanitize footwear in a user-friendly manner.

Accordingly, what is needed is a footwear cleaning system that effectively removes contaminants from one or more of the sole and other exterior surfaces of the footwear in a power-driven system that reduces the manual labor required for sanitization. However, in view of the art considered as a whole at the time the present invention was made, it was not obvious to those of ordinary skill in the field of this invention how the shortcomings of the prior art could be overcome.

All referenced publications are incorporated herein by reference in their entirety. Furthermore, where a definition or use of a term in a reference, which is incorporated by reference herein, is inconsistent or contrary to the definition of that term provided herein, the definition of that term provided herein applies and the definition of that term in the reference does not apply.

While certain aspects of conventional technologies have been discussed to facilitate disclosure of the invention, Applicant in no way disclaims these technical aspects, and it is contemplated that the claimed invention may encompass one or more of the conventional technical aspects discussed herein.

The present invention may address one or more of the problems and deficiencies of the prior art discussed above. However, it is contemplated that the invention may prove useful in addressing other problems and deficiencies in a number of technical areas. Therefore, the claimed invention should not necessarily be construed as limited to addressing any of the particular problems or deficiencies discussed herein.

In this specification, where a document, act or item of knowledge is referred to or discussed, this reference or discussion is not an admission that the document, act or item of knowledge or any combination thereof was at the priority date, publicly available, known to the public, part of common general knowledge, or otherwise constitutes prior art under the applicable statutory provisions; or is known to be relevant to an attempt to solve any problem with which this specification is concerned.

BRIEF SUMMARY OF THE INVENTION

The long-standing but heretofore unfulfilled need for a footwear cleaning system is now met by a new, useful, and nonobvious invention.

The novel system includes a housing having a front end opposite a rear end. The housing includes one or more discontinuous external walls and an interior bottom surface. The one or more discontinuous external walls define a channel within the front end of the housing. The one or more external walls and the interior bottom surface defining an internal compartment formed therebetween, with the channel providing access to the internal compartment. The internal compartment is configured to receive an item of footwear via the channel.

A lever is disposed at the front end of the housing beneath the channel defined within the housing, with the lever being in communication with a motor. A drive shaft includes a first end that is coupled to the motor and includes an opposing second end that is secured to a central gear. Upon receiving an actuation force, the lever actuates the motor.

One or more cleaning disk gears are coupled to the central gear, such that a rotation of the central gear results in a rotation of the cleaning disk gear(s). A pin is coupled to each cleaning disk gear, with the pin extending in a direction away from the cleaning disk gear and terminating at a point within the internal compartment of the housing. In an embodiment, the pin is polygonal in shape.

In an embodiment, a first cleaning disk gear and a second cleaning disk gear are disposed on diametrically opposing sides of the central gear. An intermediary gear is disposed between the first cleaning disk gear and the central gear, such that the first cleaning disk gear and the central gear are configured to rotate in the same direction, and such that the second cleaning disk gear and the intermediary gear is configured to rotate in the same direction. As such, the first cleaning disk gear and the second cleaning disk gear are configured to rotate in opposite directions.

One or more cleaning disks are removably disposed within the internal compartment of the housing. Each cleaning disk defines a central receipt that includes an associated polygonal shape that is complementary to that of the pin, such that the pin is receivable within the central receipt. Each cleaning disk includes a plurality of alternating sections of bristles and pads. For example, in an embodiment, the cleaning disk includes a first section including a plurality of bristles extending in a direction away from a top surface of the cleaning disk, such that the plurality of bristles terminate at a first height with respect to the interior bottom surface of the housing. In addition, the cleaning disk includes a second section that is disposed adjacent to the first section. The second section includes a pad having a planar top contact surface that is disposed at a second height with respect to the interior bottom surface of the housing, with the second height being less than the first height. The plurality of bristles and the planar top contact surface of the pad are configured to synergistically remove contaminants from the item of footwear by the plurality of bristles loosening contaminants from a bottom surface of the item of footwear, and by the top contact surface of the pad translating the loosened contaminants in a direction away from the item of footwear.

In an embodiment, the first section of the cleaning disk is made of a flexible material having a hardness of between approximately 25 and 40 Shore A. In an embodiment, the second section of the cleaning disk is made of an open cell foam material selected from the group consisting of reticulated polyurethane foam, urethane foam, polyethylene foam, neoprene foam, silicone foam, and combinations thereof.

An embodiment of the system includes one or more fluid reservoirs disposed within the housing and one or more dispensing nozzles disposed proximate to the front end of the housing. In an embodiment including a first and second dispensing nozzle, each dispensing nozzle is spaced apart from an opposing dispensing nozzle on an opposing side of the housing. In addition, a fluid flow system includes a first fluid conduit between the first fluid reservoir and the first dispensing nozzle, and a second fluid conduit between the second fluid reservoir and the second dispensing nozzle. In an embodiment, an intermediary conduit that is fluidically coupled to each of the first dispensing nozzle and the second dispensing nozzle, forming an intermediary component between the first and second fluid reservoirs and the first and second dispensing nozzles. As such, fluid from each of the first fluid reservoir and the second fluid reservoir is configured to be dispensed into the housing via both the first dispensing nozzle and the second dispensing nozzle.

An embodiment of the housing includes a drainage hole formed within the interior bottom surface of the housing, with the drainage hole being disposed proximate to the front end of the housing. A tray defining a fluid receptacle is removably disposed within the housing and resides beneath the interior bottom surface of the housing. The tray includes a top surface that defines a void therethrough, such that the void of the tray and the drainage hole of the housing are aligned when the tray is disposed within the housing, and such that the fluid receptacle of the tray is configured to receive and retain fluid from the housing via the drainage hole and the void. In an embodiment including a first cleaning disk and a second cleaning disk, the drainage hole is formed within the interior bottom surface of the housing between the first cleaning disk and the second cleaning disk.

In an embodiment, the system includes one or more rotating buffers that are disposed between the back end of the housing and the cleaning disk. Each rotating buffer is attached to opposing sides of the housing and is configured to contact one or more of a top surface and a toe-end surface of the item of footwear. For example, in an embodiment, a first rotating buffer is configured to be disposed proximate to a toe-end of an item of footwear and a second rotating buffer is configured to be disposed proximate to a top surface of the item of footwear, such that the second rotating buffer is located above the first rotating buffer with respect to the interior bottom surface of the housing. In an embodiment, each rotating buffer is biconcave cylindrical in shape such that the rotating buffer includes a contacting surface that is configured to conform to one or more of the top surface and the toe-end surface of the item of footwear.

In an embodiment, a pair of opposing pivotable arms are disposed on opposite sides of the housing. Each rotating buffer includes a projection extending from opposing sides thereof. Each of the pair of opposing pivotable arms define a receipt that is configured to receive one of the projections of the rotating buffer. As such, a position of the rotating buffer is selectable by translating the projections within the receipts.

An embodiment of the system includes a transparent section of the interior bottom surface of the housing. A plurality of ultraviolet light sources are disposed beneath the transparent section of the interior bottom surface of the housing and are oriented to emit ultraviolet light through the transparent section and into the internal compartment of the housing.

An object of the invention is to provide a comprehensive and synergistic cleaning system for an item of footwear, such that a shoe or similar item can be placed within a compartment and can receive fluid and/or scrubbing-based cleaning to remove contaminants from the item of footwear, thereby efficiently and effectively sanitizing the item to prevent contaminant spread.

These and other important objects, advantages, and features of the invention will become clear as this disclosure proceeds.

The invention accordingly comprises the features of construction, combination of elements, and arrangement of parts that will be exemplified in the disclosure set forth hereinafter and the scope of the invention will be indicated in the claims.

BRIEF DESCRIPTION OF THE DRAWINGS

For a fuller understanding of the invention, reference should be made to the following detailed description, taken in connection with the accompanying drawings, in which:

FIG. 1B is a rear orthogonal view of the footwear cleaning system of FIG. 1A.

FIG. 4B is an exploded perspective view of the attachment mechanism of FIG. 4A and a gear and motor mechanism in communication with the attachment mechanism, in accordance with an embodiment of the present invention.

FIG. 5B is an orthogonal view of the buffer component of FIG. 5A, shown secured to an attachment point of a housing of the footwear cleaning system, in accordance with an embodiment of the present invention.

FIG. 6B is an orthogonal view of the footwear cleaning system of FIG. 6A showing the actuating lever in an in-use configuration, in accordance with an embodiment of the present invention.

DETAILED DESCRIPTION OF THE INVENTION

Figure 1A:
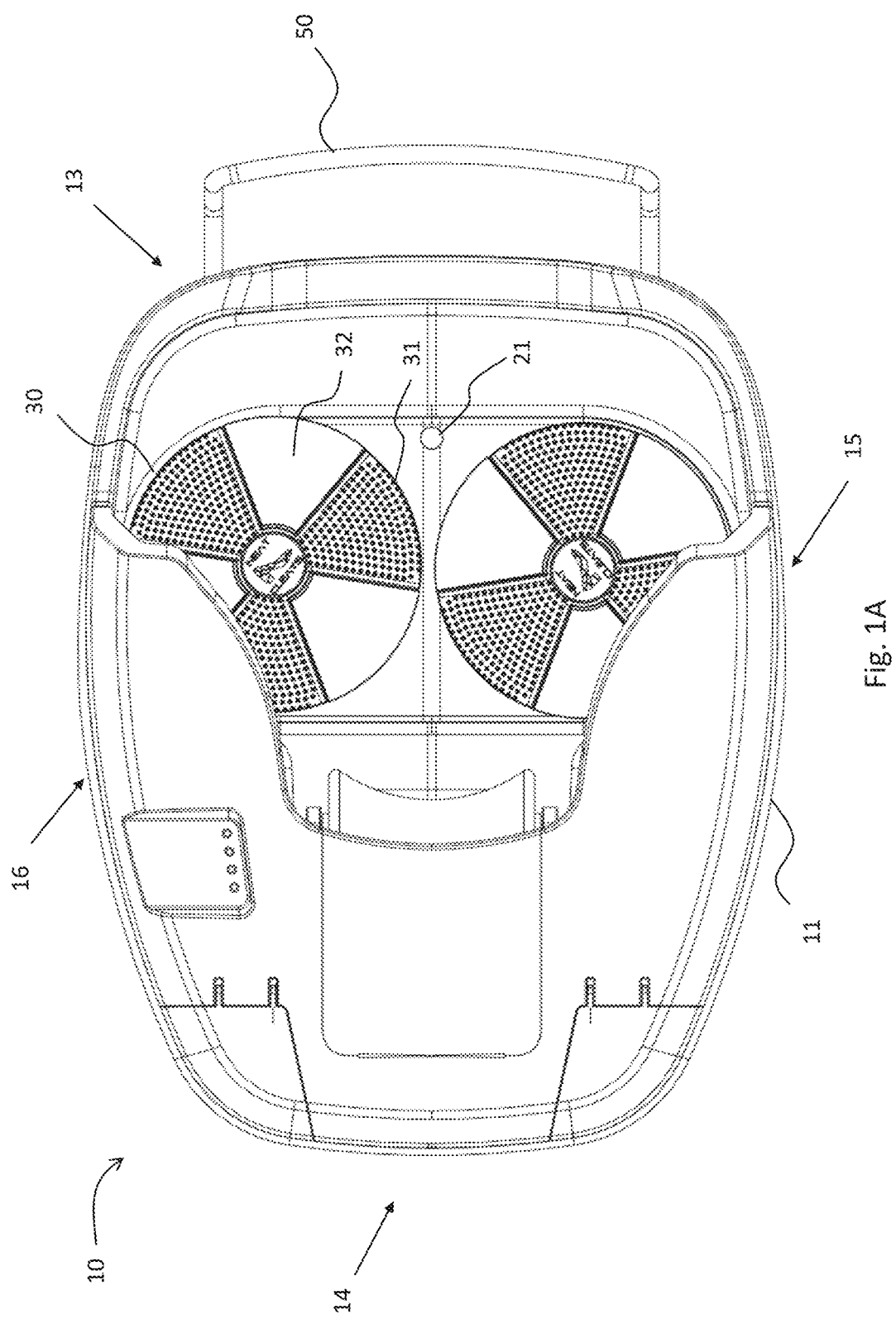
FIG. 1A is a top plan view of a footwear cleaning system, in accordance with an embodiment of the present invention.
Figure 1C:
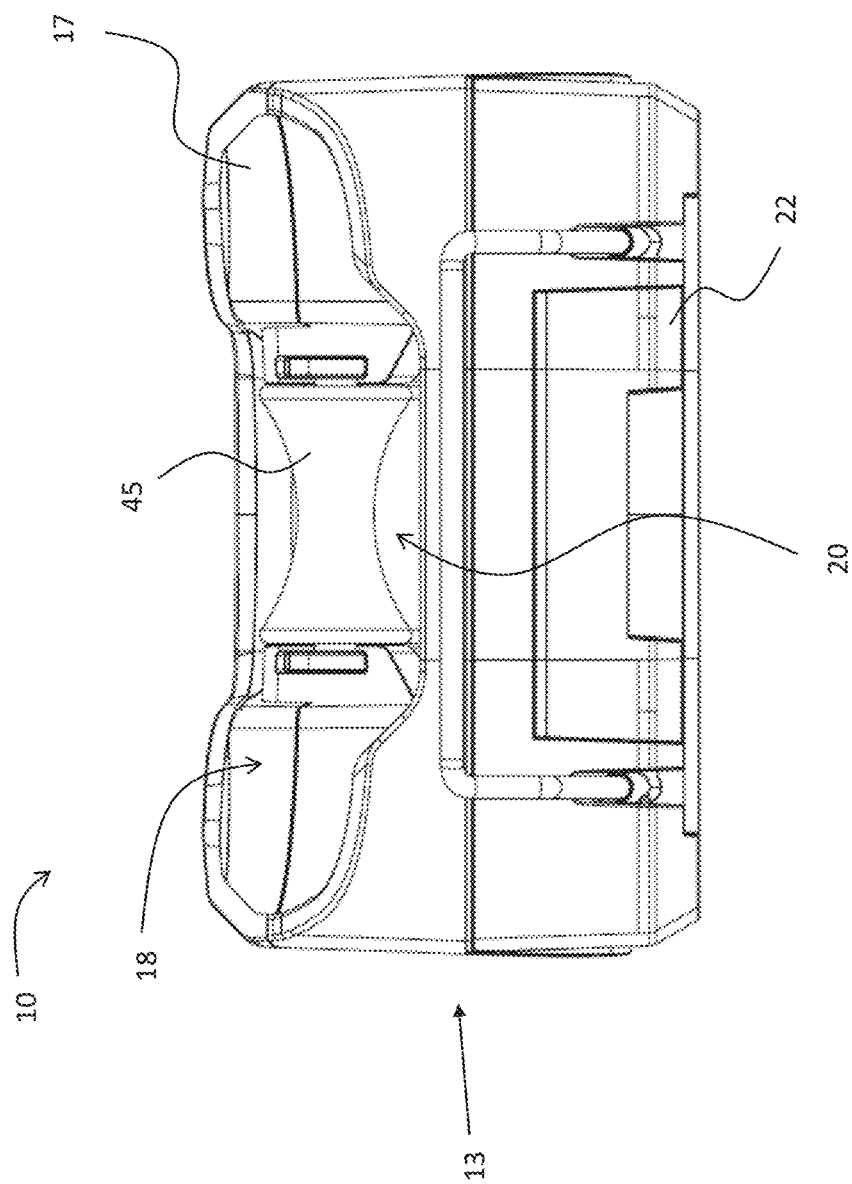
FIG. 1C is front orthogonal view of the footwear cleaning system of FIG. 1A.
Figure 1D:
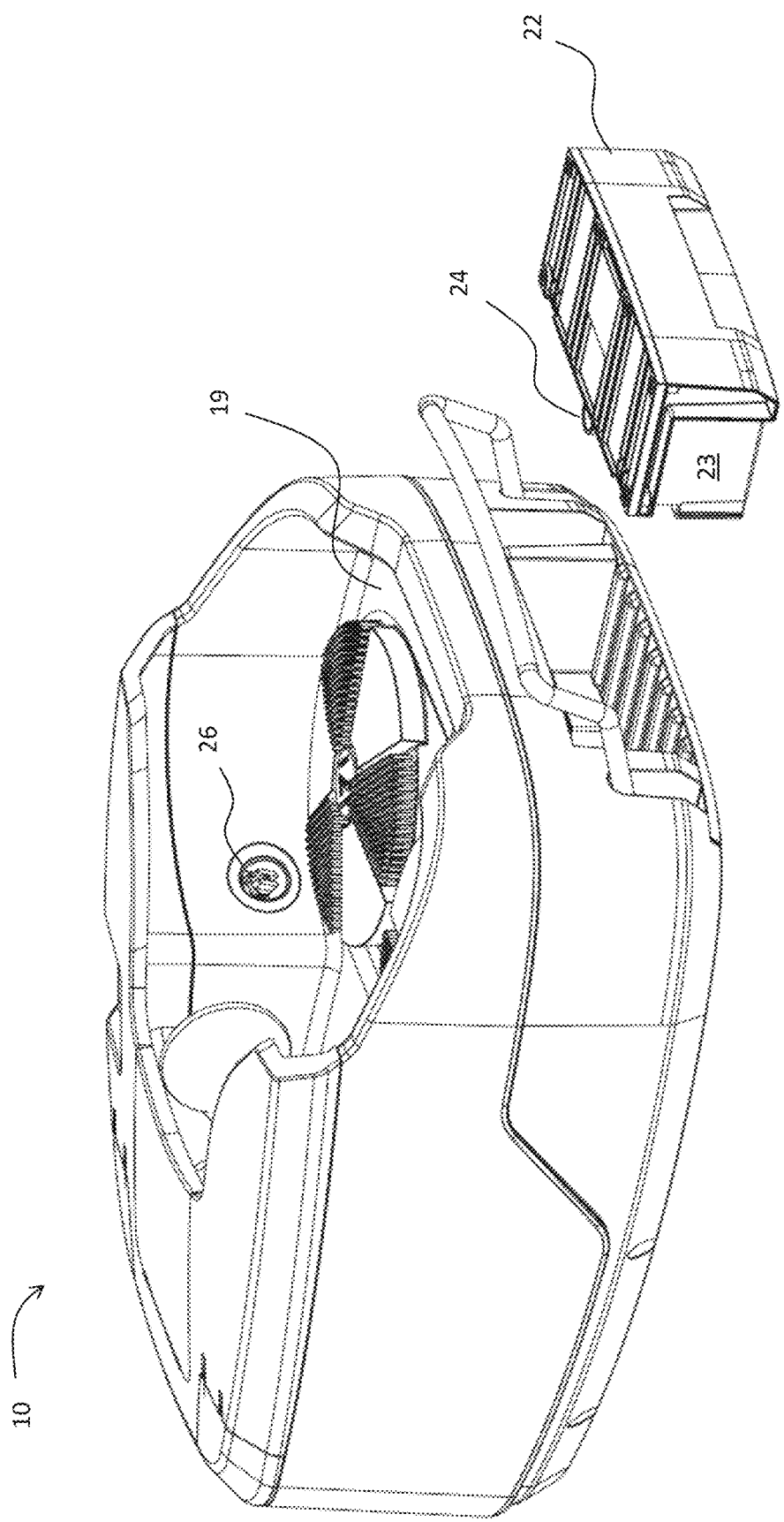
FIG. 1D is a perspective view of the footwear cleaning system of FIG. 1A with a removable tray shown in a removed position disposed away from the housing of the system, in accordance with an embodiment of the present invention.

In the following detailed description of the preferred embodiments, reference is made to the accompanying drawings, which form a part thereof, and within which are shown by way of illustration specific embodiments by which the invention may be practiced. It is to be understood that other embodiments may be utilized and structural changes may be made without departing from the scope of the invention.

As used in this specification and the appended claims, the singular forms "a," "an," and "the" include plural referents unless the content clearly dictates otherwise. As used in this specification and the appended claims, the term "or" is generally employed in its sense including "and/or" unless the context clearly dictates otherwise.

All numerical designations are approximations which are varied up or down by increments of 1.0 or 0.1, as appropriate. It is to be understood, even if it is not always explicitly stated that all numerical designations are preceded by the term "about." As used herein, "about" or "approximately" refers to being within an acceptable error range for the particular value as determined by one of ordinary skill in the art, which will depend in part on how the value is measured or determined. As used herein, the terms "about" and "approximately" refer to ±10% of the numerical; it should be understood that a numerical including an associated range with a lower boundary of greater than zero must be a non-zero numerical, and the terms "about" and "approximately" should be understood to include only non-zero values in such scenarios.

The phrases "in an embodiment," "in some embodiments," "according to some embodiments," "in the embodiments shown," "in other embodiments," and the like generally mean the particular feature, structure, or characteristic following the phrase is included in at least one implementation. In addition, such phrases do not necessarily refer to the same embodiments or different embodiments.

The present invention includes a footwear cleaning system that includes an outer housing that encases an internal compartment, which is designed, sized, and shaped to receive a footwear item therein, such as an athletic shoe, dress shoe, platform shoe, or other similar footwear item. In some embodiments, the footwear cleaning system includes one or more rotatable cleaning disks disposed within the internal compartment, such that the cleaning disks are configured to interact with a bottom surface of a footwear item. In some embodiments, the footwear cleaning system includes one or more fluidic conduits that terminate at a location that is proximate to the internal compartment, such that water, cleaning solutions, concentrated cleaning products, alcohol, and other fluids can be dispelled into the internal compartment to interact with a footwear item. Embodiments of the footwear cleaning system will be discussed herein below.

As shown in FIGS. 1A-1D, the footwear cleaning system 10 (alternatively referred to herein as the "system" or the "cleaning system") includes one or more exterior walls 11 that form a housing 12 including a front end 13 that is opposite a back end 14. In addition, one or more lateral interior surfaces 17 of the wall(s) partially defining an internal compartment 18. The internal compartment 18 is also defined by an interior bottom surface 19 that is approximately perpendicular to the one or more lateral interior surfaces 17, such that the internal compartment 18 is defined by the space between the one or more lateral interior surfaces 17 and the interior bottom surface 19 of the housing 12. In an embodiment, a lid forms a top surface of the housing 12, with the lid being approximately parallel to the interior bottom surface 19 and approximately perpendicular to the one or more exterior walls 11 of the housing 12. The lid may be pivotably attached to one or more surfaces of the housing, such as the one or more exterior walls 11, such that the lid is configured to pivot to be approximately perpendicular to the interior bottom surface 19 of the housing 12 in a pivoted configuration.

The one or more exterior walls 11 of the housing 12 are discontinuous, such that a void exists at the front end 13 of the housing 12. The void forms a channel 20 that is defined within the housing 12, with the channel 20 providing access to the internal compartment 18 from an exterior environment surrounding the housing 12. As such, the internal compartment 18 is configured to receive an item to be cleaned therein, such as an item of footwear. Moreover, the channel 20 is configured such that the item to be cleaned within the internal compartment 18, such as the item of footwear, is insertable through the channel 20 to be at least temporarily disposed within the internal compartment 18. Accordingly, the internal compartment 18 of the housing 12 is configured to form a cleaning location of the footwear cleaning system 10, within which the item to be cleaned resides during a cleaning process.

The interior bottom surface 19 of the housing 12 defines a drainage hole 21 that is disposed proximate to the front end 13 of the housing 12. The drainage hole 21 forms a channel 20 to a removable tray 22 that is disposed beneath the interior bottom surface 19, which will be described in greater detail below. In an embodiment, the interior bottom surface 19 of the housing 12 is sloped from the back end 14 to the front end 13, such that the front end 13 is disposed at a point in space that is beneath an associated point in space of the back end 14. As such, in the absence of an external force, any fluid that is disposed within the housing 12 translates from the back end 14 to the front end 13 as a result of the slope toward the front end 13, such that the fluid translates in a direction toward the drainage hole 21.

As noted above, a removable tray 22 is disposed beneath the interior bottom surface 19 of the housing 12, with the removable tray 22 being in fluidic communication with the internal compartment 18 defined by the housing 12 via the drainage hole 21 defined within the interior bottom surface 19. The removable tray 22 includes one or more exterior lateral walls, a bottom surface, and a discontinuous top surface that define a fluid receptacle 23. The discontinuous top surface of the removable tray 22 defines a void 24 that is approximately aligned with the drainage hole 21 defined by the interior bottom surface 19 of the housing 12, such that fluid disposed within the internal compartment 18 of the housing 12 can flow into the removable tray 22 via the drainage hole 21 and the void 24 defined by the top surface of the removable tray 22. As such, fluid from the internal compartment 18 can flow into the fluid receptacle 23, thereby removing excess fluid from the internal compartment 18 during a cleaning process, as will be described in greater detail below.

In addition, the removable tray 22 is selectively removable from the housing 12, such that any fluid disposed within the fluid receptacle 23 can be removed from the entire footwear cleaning system 10. In an embodiment, at least one of the one or more exterior lateral walls of the removable tray 22 forms at least a portion of the exterior lateral walls of the housing 12. Accordingly, the removable tray 22 is configured such that a user can interact with the removable tray 22 from the front end 13 of the housing 12, thereby removing the removable tray 22 for fluid disposal, and replacing the removable tray 22 within the body of the housing 12.

Figure 2A:
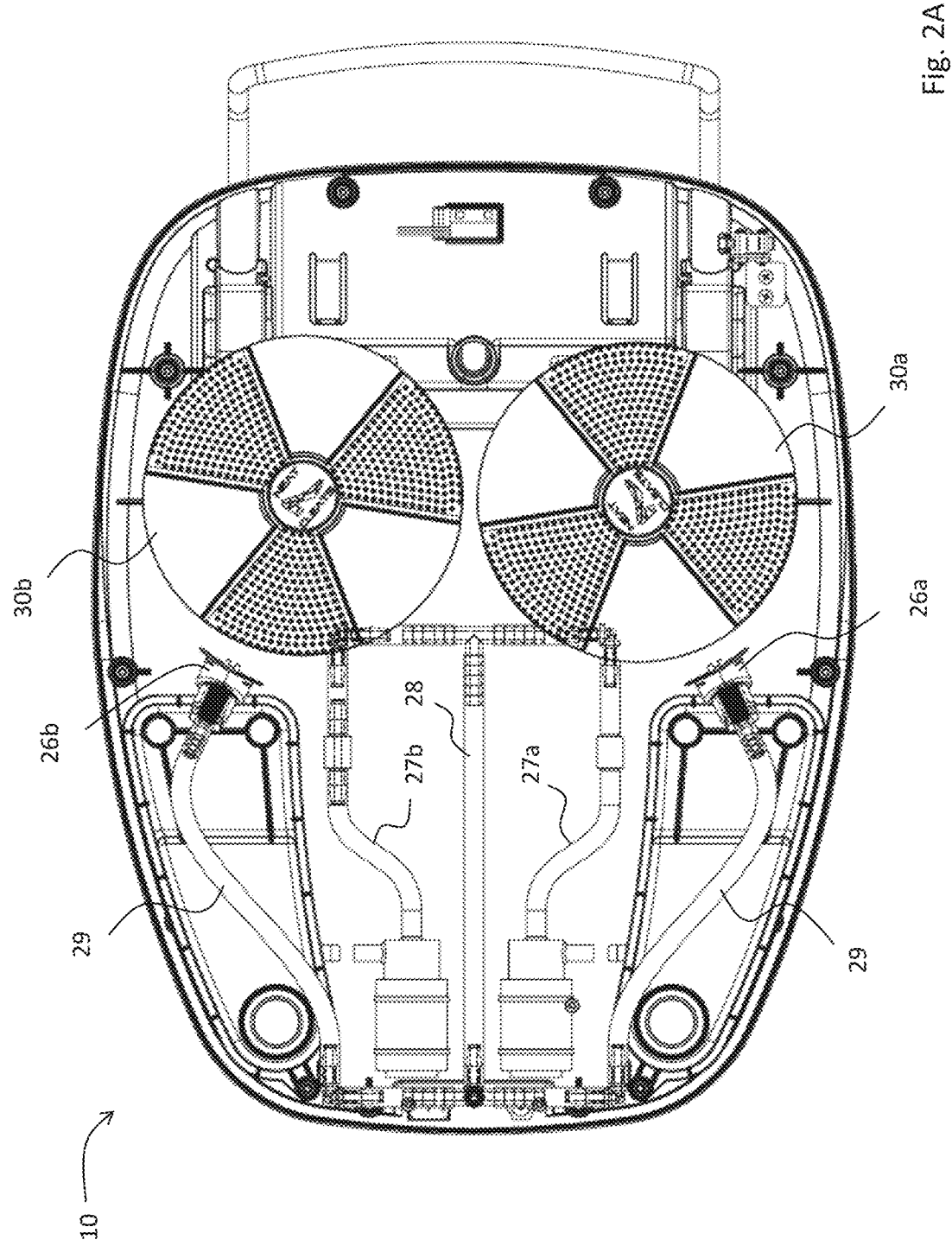
FIG. 2A is a top plan internal view of a footwear cleaning system, in accordance with an embodiment of the present invention.
Figure 2B:
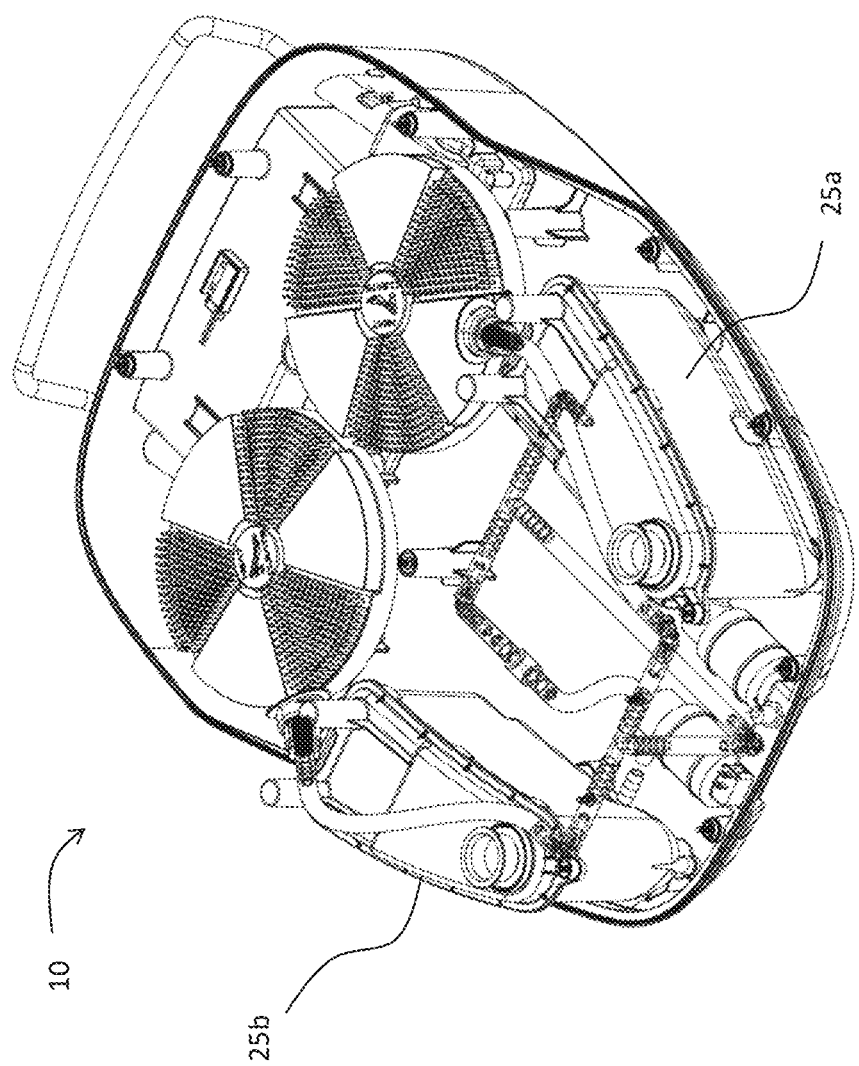
FIG. 2B is a perspective internal view of the footwear cleaning system of FIG. 2A.
Figure 2C:
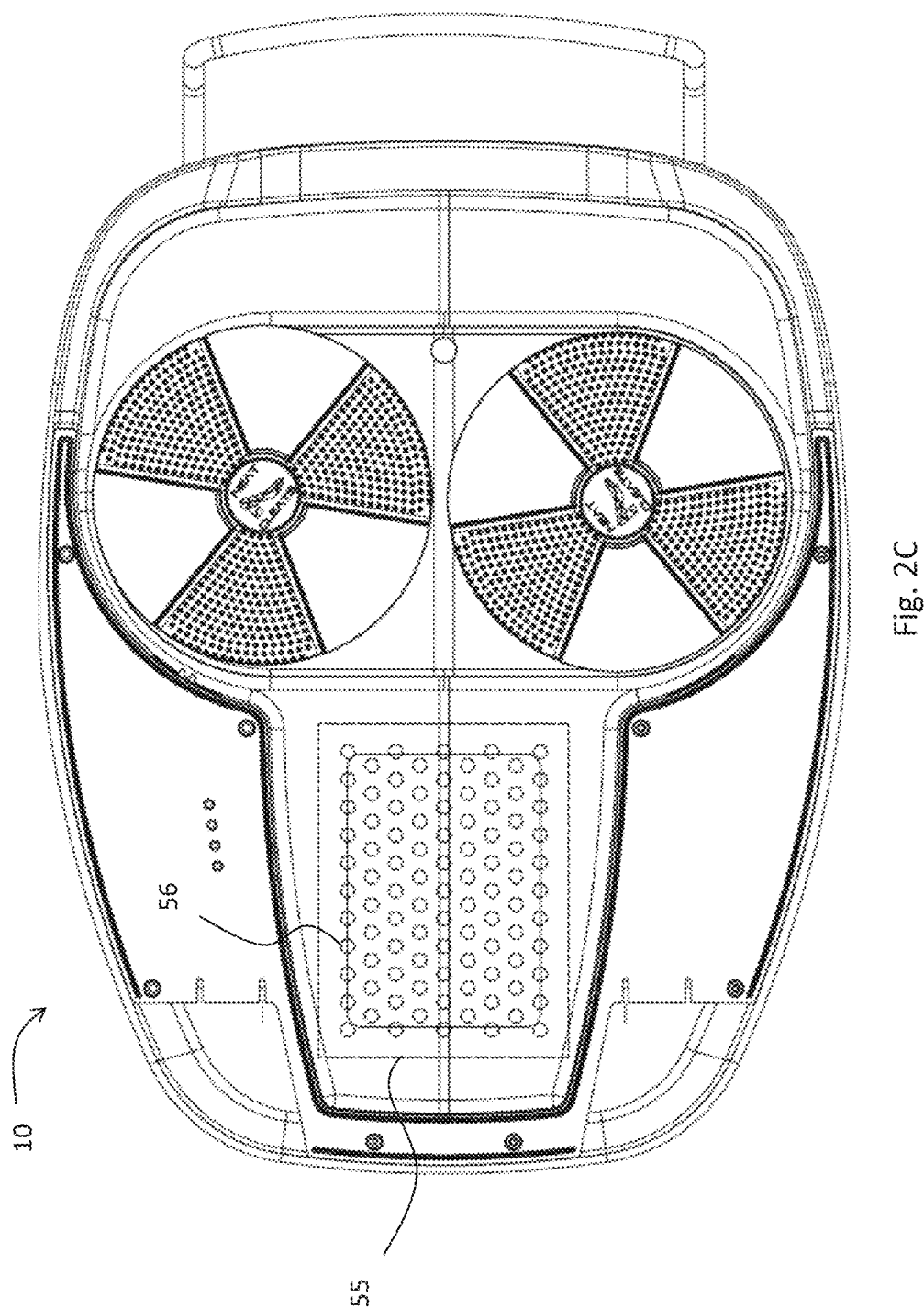
FIG. 2C is a top plan internal view of a footwear cleaning system showing a plurality of ultraviolet light sources, in accordance with an embodiment of the present invention.
Figure 3A:
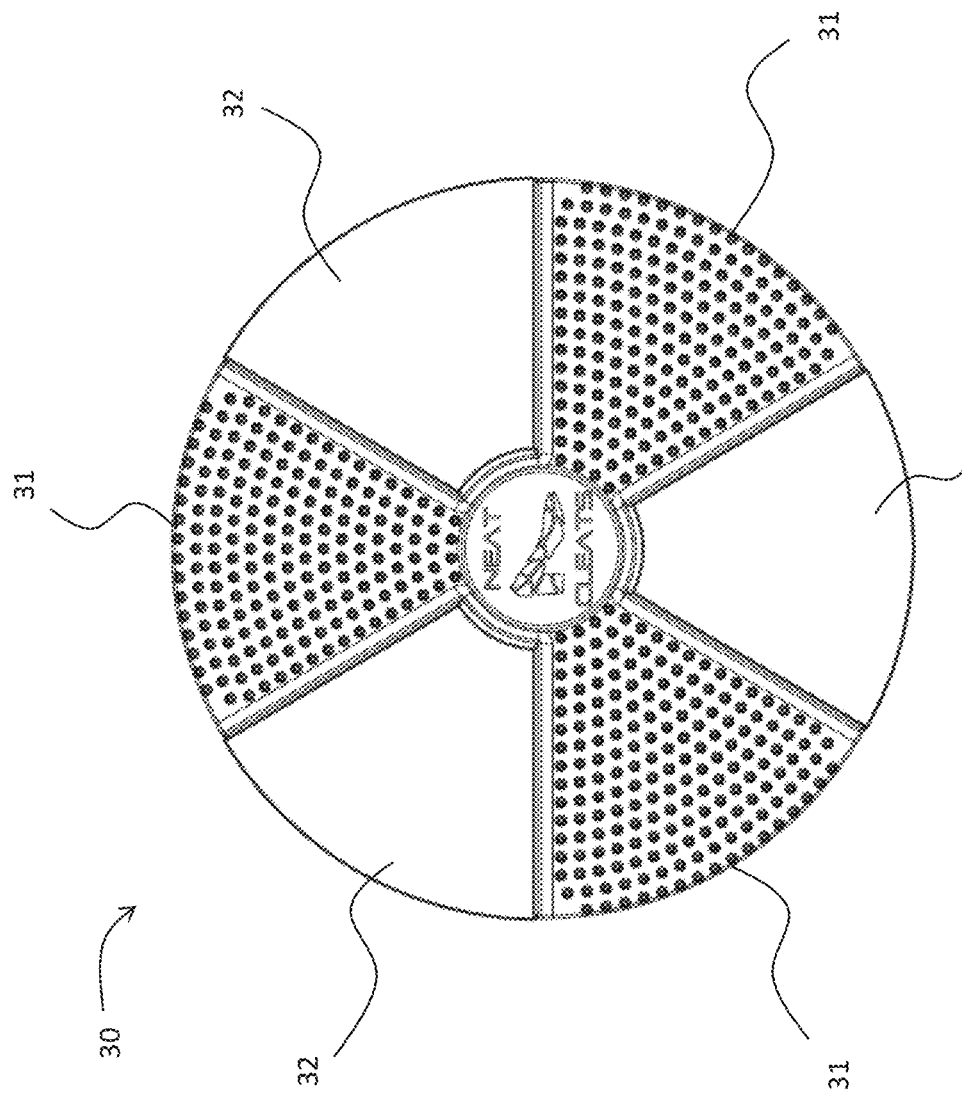
FIG. 3A is a top plan view of a cleaning disk used in combination with a footwear cleaning system, in accordance with an embodiment of the present invention.
Figure 3B:
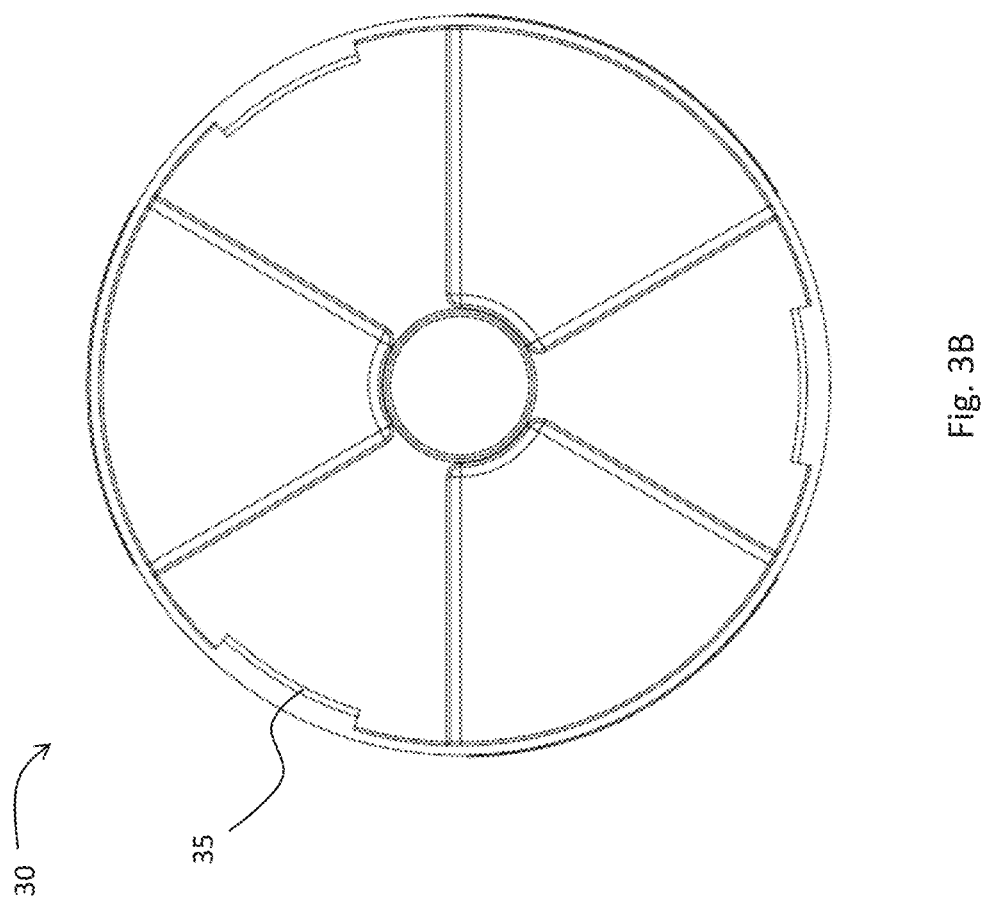
FIG. 3B is a bottom plan view of the cleaning disk of FIG. 3A.
Figure 3C:
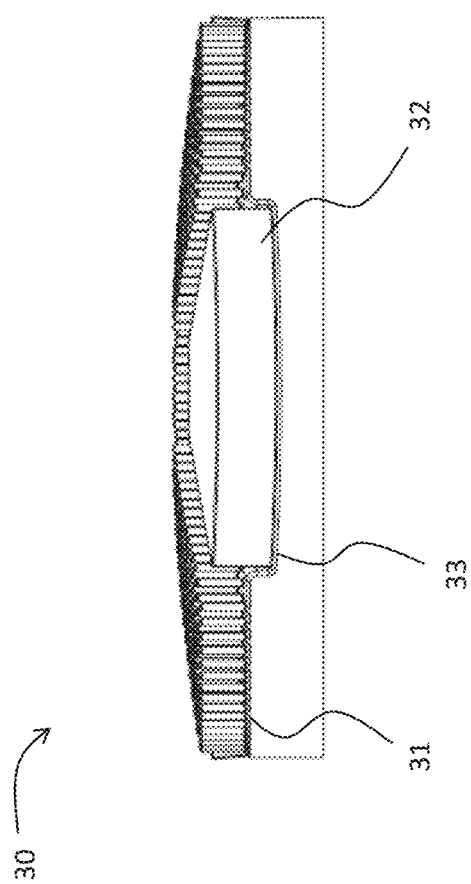
FIG. 3C is an orthogonal view of the cleaning disk of FIG. 3A.
Figure 3D:
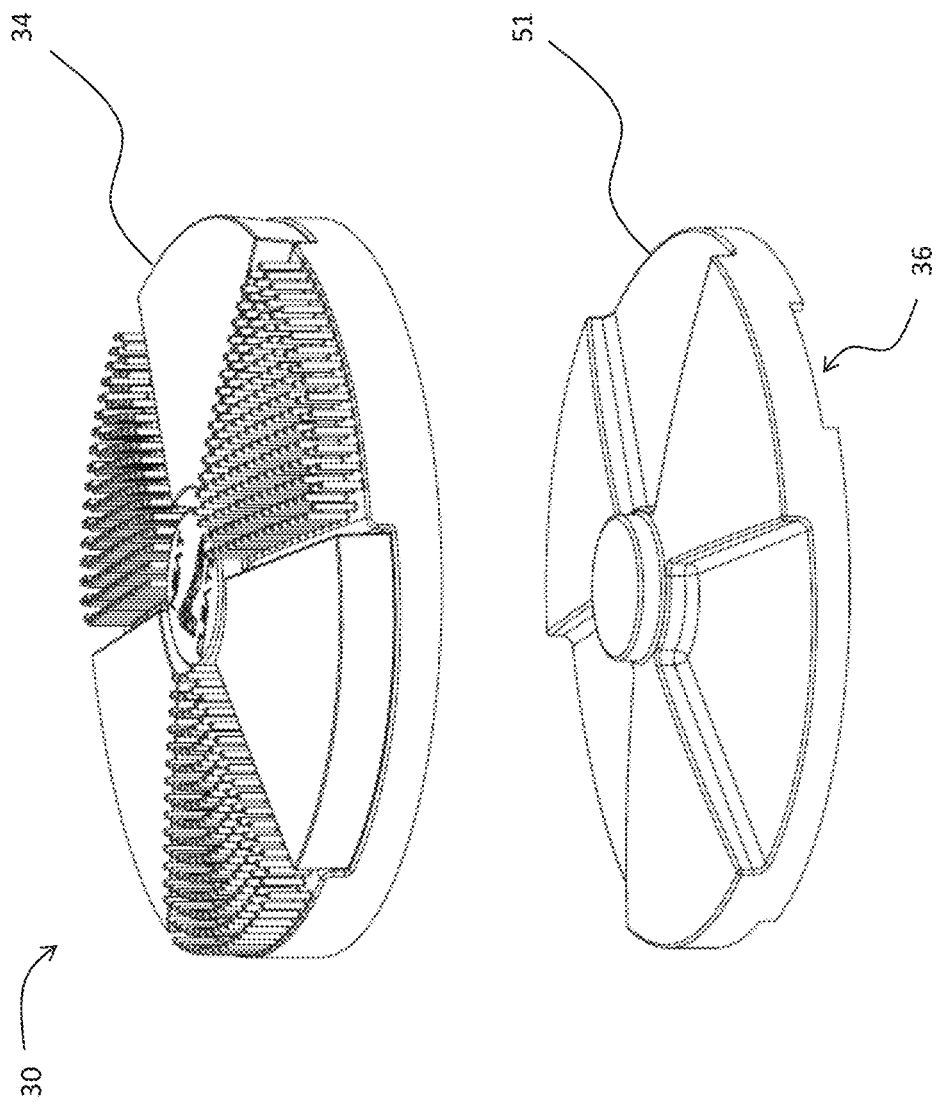
FIG. 3D is a top perspective view of the cleaning disk of FIG. 3A shown in combination with an anchoring platform that is designed to couple to the cleaning disk, in accordance with an embodiment of the present invention.
Figure 3E:
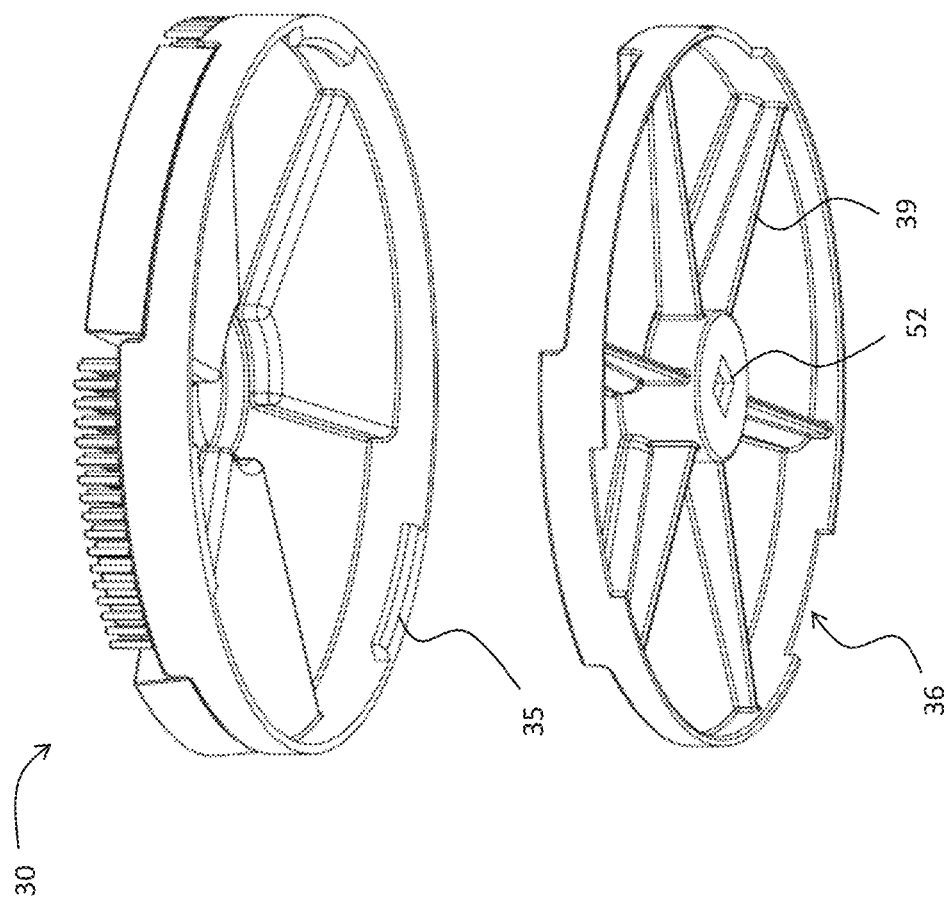
FIG. 3E is a bottom perspective view of the cleaning disk and the anchoring platform of FIG. 3D.

Referring to FIGS. 2A-2C, in combination with FIGS. 1A-1D, one or more fluid reservoirs 25, or fluid tanks, are in fluidic communication with the internal compartment 18 of the housing 12. For example, in an embodiment, a first dispensing nozzle 26a is disposed within the housing 12 such that the first dispensing nozzle 26a is directed toward the internal compartment 18 of the housing 12, such that fluid that is dispensed from the first dispensing nozzle 26a is disposed within the internal compartment 18 of the housing 12. The first dispensing nozzle 26a is in fluidic communication with a first fluid reservoir 25a that is spaced apart from the internal compartment 18 of the housing 12; for example, an embodiment of the first fluid reservoir 25a resides adjacent to the internal compartment 18 of the housing 12, with a separation wall forming a barrier between the first fluid reservoir 25a and the internal compartment 18. In another embodiment, the first fluid reservoir 25a is disposed beneath the internal compartment 18 and is spaced apart from the removable tray 22, such that direct fluid flow does not occur between the first fluid reservoir 25a and the removable tray 22.

The first fluid reservoir 25a is fluidically coupled to the first dispensing nozzle 26a via a first fluid conduit 27a. In an embodiment, the first fluid conduit 27a secures to the first fluid reservoir 25a at a first end and secures to the first dispensing nozzle 26a at an opposing second end. In another embodiment, the first fluid conduit 27a secures to the first fluid reservoir 25a at a first end and secures to an intermediary conduit 28 at an opposing second end, with the intermediary conduit 28 being fluidically coupled to the first dispensing nozzle 26a. As such, fluid that is disposed within the first fluid reservoir 25a travels in a direction toward the first dispensing nozzle 26a via the first fluid conduit 27a, such that fluid within the first fluid reservoir 25a interacts with an item of footwear within the internal compartment 18 of the housing 12 after being dispensed by the first dispensing nozzle 26a.

In an embodiment, the footwear cleaning system 10 includes a second fluid reservoir 25b that is in fluidic communication with the internal compartment 18 of the housing 12 via a second dispensing nozzle 26b that is spaced apart from the first dispensing nozzle 26a. More particularly, the first dispensing nozzle 26a is disposed on a first side 15 of the housing 12, and the second dispensing nozzle 26b is disposed on a second side 16 of the housing 12, such that the first dispensing nozzle 26a is configured to direct fluid toward a first side of a footwear item, and such that the second dispensing nozzle 26b is configured to direct fluid toward a second side of the footwear item. In addition, each of the first and second dispensing nozzles 26 is rotatable within an associated nozzle housing to selectively alter a spray angle of the associated dispensing nozzle 26, as well as to alter a spray type of the fluid emitted from the dispensing nozzle 26. It should be appreciated that a plurality of dispensing nozzles 26 can be used within the system 10 and can be disposed within the housing 12 at different locations, such as disposed proximate to the back end 14 of the housing 12.

Similar to the first dispensing nozzle 26a described in detail above, the second dispensing nozzle 26b is in fluidic communication with a second fluid reservoir 25b that is spaced apart from the internal compartment 18 of the housing 12, and that is spaced apart from the first fluid reservoir 25a. For example, in an embodiment of the system 10, the first fluid reservoir 25a is disposed on a first side 15 of the housing 12 and the second fluid reservoir 25b is disposed on a second side 16 of the housing 12. In an embodiment, each of the first and second fluid reservoirs 25 includes a lid that is removable or translatable (such as via a hinge) to provide access from an exterior environment of the housing 12 to each reservoir 25, thereby allowing each of the first and second fluid reservoirs 25 to be cleaned, refilled, or replaced.

In addition, similar to the first fluid flow system including the first fluid reservoir 25a, the first fluid conduit 27a, and the first dispensing nozzle 26a, a second fluid flow system includes the second fluid reservoir 25b, the second dispensing nozzle 26b, and a second fluid conduit 27b. Similar to the first fluid conduit 27a, an embodiment of the second fluid conduit 27b secures to the second fluid reservoir 25a at a first end and secures to the second dispensing nozzle 26b at an opposing second end. In another embodiment, the second fluid conduit 27b secures to the second fluid reservoir 25b at a first end and secures to an intermediary conduit 28 at an opposing second end, with the intermediary conduit 28 being fluidically coupled to the second dispensing nozzle 26b. As such, fluid that is disposed within the second fluid reservoir 25b travels in a direction toward the second dispensing nozzle 26b via the second fluid conduit 27b, such that fluid within the second fluid reservoir 25b interacts with an item of footwear within the internal compartment 18 of the housing 12 after being dispensed by the second dispensing nozzle 26b. To accommodate for items of footwear and other items to be cleaned within the housing 12 having varying sizes and dimensions, one or more of the first and second dispensing nozzles 26 are rotatable to change a dispensing angle associated with the nozzle.

As noted above, embodiments of the system 10 include one or more intermediary conduits 28 between the first and second fluid conduits 27 and respective nozzles 26 of the system 10. The intermediary conduit(s) 28 allow for the fluid from the first fluid reservoir 25a to be dispensed through each of the first dispensing nozzle 26a and the second dispensing nozzle 26b. Similarly, the intermediary conduit (s) 28 allow for the separate dispensing of the fluid from the second fluid reservoir 25b from each of the first and second dispensing nozzles 26. In such embodiments, the first fluid conduit 27a from the first fluid reservoir 25a terminates at the intermediary conduit 28, which includes branching conduits 29 terminating at each of the first dispensing nozzle 26a and the second dispensing nozzle 26b. Similarly, the second fluid conduit 27b from the second fluid reservoir 25b terminates at the intermediary conduit 28, with the branching conduits 29 of the intermediate conduit 28 terminating at each of the first and second dispensing nozzles 26. As such, the system 10 utilizes both the first and second dispensing nozzles 26 to dispense fluid from each reservoir 25, thereby subjecting an item of footwear to fluid from each reservoir 25 on each side of the footwear item.

Each fluid reservoir 25 that is included in the system 10 is configured to receive and store fluid therein, and pump an amount of the fluid to one or more of the dispensing nozzles 26 for use within the system 10. Depending on the requirements of the system 10, various fluids can be used in the cleaning of an item of footwear within the internal compartment 18 of the housing 12. For example, an embodiment of the first fluid reservoir 25a includes a liquid solution including one or more surfactants, such as a detergent, that is used to subject the item of footwear to a cleaning agent to remove one or more contaminants from the footwear item. In addition, an embodiment of the second fluid reservoir 25b includes water or a diluted alcohol-based solution that is used to subject the item of footwear to a rinsing and/or drying step after being washed with a detergent from the first fluid reservoir 25a. It should be appreciated that different cleaning, rinsing, and drying fluids can be stored within and dispensed from one or more of the first and second fluid reservoirs 25, and that additional fluid reservoirs 25 can be used in combination with the system 10.

Referring to FIGS. 3A-3E in particular, in combination with FIGS. 1A-1D and 2A-2C, in addition to the fluid-based cleaning described in detail above, the system 10 includes one or more cleaning disks 30 that are disposed within the internal compartment 18 of the housing 12 and are configured to contact a bottom surface of an item of footwear. Each cleaning disk 30 is anchored to the interior bottom surface 19 of the housing 12, such that each cleaning disk 30 is configured to reside beneath the footwear item in an in-use configuration of the system 10, with the footwear item being received within the internal compartment 18 of the housing 12. In an embodiment, two opposing cleaning disks 30 are disposed within the housing 12, with a first cleaning disk 30a being located on a first side 15 of the housing 12, and an opposing second cleaning disk 30b being located on a second side 16 of the housing 12. In some embodiments, the drainage hole 21 that is formed within the interior bottom surface 19 of the housing 12 is disposed between the first and second cleaning disks 30.

Each cleaning disk 30 includes one or more alternating sections of flexible bristles 31 and of a pad 32 having an approximately flat top contact surface; for example, in an embodiment, the cleaning disk 30 includes a section of flexible bristles 31 that occupies approximately half of the cleaning disk 30, with an adjacent section of a pad 32 having a flat contact surface that occupies the remining half of the cleaning disk 30. In another embodiment, the cleaning disk 30 includes four approximately equal sections of alternating flexible bristles 31 and pads 32; in other embodiments, six sections of alternating flexible bristles 31 and pads 32 form the cleaning disk 30, and in still other embodiments, eight or more sections of alternating flexible bristles 31 and pads 32 form the cleaning disk 30.

Regardless of the number of alternating sections of flexible bristles 31 and pads 31, each section of flexible bristles 31 terminates at a point in space that is above a top contact surface of the pad 32 of the cleaning disk 30. For example, in an embodiment, approximately each bristle of a section of flexible bristles 31 is disposed about one-eighth to one-quarter of an inch higher than the top contact surface of a pad 32 of the cleaning disk 30. The flexible bristles 31 terminate at a point that is higher than the pad 32 because the flexible bristles 31 are designed to bend during use, such as when the bristles contact a bottom surface of an item of footwear. As such, when each bristle 31 contacts the bottom surface of the item of footwear, the bristle 31 continuously contacts the item of footwear, bending without fracturing or breaking, and rebounding to a position of repose in the absence of a force from the item of footwear.

As noted above, each bristle 31 must be capable of bending without breaking and capable of rebounding to a position of repose. To accomplish both the in-use configuration of bending under the force of the item of footwear, as well as the non-use configuration of the position of repose, each bristle 31 must be thin enough to be capable of flexing, and thick enough to penetrate through contaminants disposed on the bottom surface of the footwear item. Accordingly, each bristle 31 includes a diameter of approximately one-sixteenth to one-eighth of an inch, thereby ensuring that the bristle 31 sufficiently penetrates the contaminants on the footwear item while simultaneously ensuring that the bristles 31 remain in continuous contact with the footwear item as the section of bristles 31 passes beneath the footwear item (i.e., without exerting an upward force on the footwear item that translates the footwear item in a direction away from the cleaning disk 30).

In addition, each bristle 31 is made of a material having a hardness of between approximately 25-40 Shore A and having antimicrobial properties and/or coatings to ensure sufficient contact with the item of footwear without breaking, fracturing, or otherwise deteriorating. Examples of the material for the bristles 31 include silicone, vulcanized rubber, butyl rubber, natural rubber, synthetic rubber, neoprene, ethylene propylene diene monomer (EPDM) rubber, nitrile polymers, hydrogenated nitrile polymers, polyurethane, combinations thereof, and similar materials that are capable of flexing upon receiving a force from an item of footwear.

Moreover, as noted above, each section of flexible bristles 31 is disposed adjacent to a pad 32 having an approximately flat top contact surface. The top contact surface of each pad 32 is configured to contact a bottom surface of a footwear item to translate loosened contaminants, such as dirt, in a direction away from the footwear item. For example, in an embodiment, a section of flexible bristles 31 first contacts the bottom surface of the footwear item to loosen one or more contaminants from the bottom surface of the item; next, a pad 32 section interacts with the loosened contaminants via the top contact surface, thereby removing the loosened contaminants from the footwear item. As such, the alternating sections of bristles 31 and pads 32 synergistically loosen and remove contaminants from the footwear item.

Since the top contact surface of each pad 32 interacts with the bottom surface of the footwear item, each pad 32 must have a volume to accommodate for potential degradation of the pad 32 during use resulting from friction forces between the pad 32 and the footwear item. As such, in an embodiment, each pad 32 has an associated height of approximately three-quarters of an inch to one inch, thereby ensuring that at least a portion of each pad 32 interacts with the bottom surface of the footwear item. Moreover, embodiments of the one or more pads 32 are made of an open cell foam, such that the pad 32 is resilient and difficult to de-bond from the cleaning disk 30, antimicrobial (to prevent mold growth and odor), inert enough to prevent degradation in the presence of alcohol (such as with embodiments of the fluid flow system that utilize alcohol as a drying fluid), and strong enough to retain an initial shape without degradation or alterations via downward forces exerted on the pads 32 by the footwear item. Examples of the open cell foam of the pads 32 include reticulated polyurethane foams, non-reticulated polyurethane foams, urethane foams including polyester and polyether, polyethylene foams, neoprene foams, silicone foams, ethylene propylene diene monomer (EPDM) rubbers, polyvinyl chloride (PVC) materials, nitrile polymers, combinations thereof, and similar open cell foam materials.

Moreover, since the top contact surface of each pad 32 exerts a force on the bottom surface of the footwear item and receives a force exerted by the bottom surface of the footwear item, it is important to ensure that each pad 32 is prevented from relative linear movement resulting from the exerted and received forces. As such, each cleaning disk 30 includes one or more indentations 33 formed therein and defined by opposing lateral side walls that are joined together by a longitudinal bottom wall. Each of the pads 32 is configured to be received within one of the indentations 33, with the lateral side walls preventing linear translation of each pad 32 during contact with the bottom surface of the footwear item. In an embodiment, the cleaning disk 30 is a singular component that includes the indentations 33, pad sections 32, and bristle sections 31, such that the entire cleaning disk 30 is removable and replaceable from within the housing 12.

In another embodiment, the cleaning disk 30 is a multi-component system that includes an anchoring platform 51 including the indentations 33 described above, with a removable and replaceable pad-and-bristle fitting 34 selectively couplable to the anchoring platform 51. As such, during replacement of a worn pad-and-bristle fitting 34, the anchoring platform 51 remains secured within the housing 12, with only the pad-and-bristle fitting 34 being removed from and replaced within the system 10. In an embodiment, the anchoring platform 51 includes one or more circumferentially disposed receipts 36 formed therein, with the pad-and-bristle fitting 34 including one or more complementary tabs 35 circumferentially extending therefrom. As such, the one or more complementary tabs 35 that extend radially away from a body of the pad-and-bristle fitting 34 is received within the one or more receipts 36, thereby securing the pad-and-bristle fitting 34 to the anchoring platform 51 to prevent relative linear or rotational movement of the pad-and-bristle fitting 34 with respect to the anchoring platform 51. It should be appreciated that an embodiment of the multi-component system can include one or more receipts 36 defined within the pad-and-bristle fitting 34 with one or more complementary tabs 35 extending radially away from a body of the anchoring platform 51 to secure the pad-and-bristle fitting 34 to the anchoring platform 51.

As noted above, each cleaning disk 30 is secured to the interior bottom surface 19 of the housing 12. For example, in an embodiment, an attachment point 37 resides within the housing 12 on the interior bottom surface 19 thereof, with the attachment point 37, also referred to as pin 37, extending perpendicularly away from the interior bottom surface 19 of the housing 12. In this embodiment, the cleaning disk 30 includes one or more lateral interior walls that define a receipt 52 formed within the cleaning disk 30, such that the pin of the attachment point 37 is receivable within the receipt 52 of the cleaning disk 30. In another embodiment, the attachment point within the housing 12 includes one or more lateral interior walls disposed within the housing 12 adjacent to the interior bottom surface 19, such that the one or more lateral interior walls of the attachment point within the housing 12 forms a receipt. In such an embodiment, the cleaning disk 30 includes a pin extending perpendicularly away therefrom, such that the pin of the cleaning disk 30 is receivable within the receipt of the attachment point disposed within the housing 12. In embodiments, the pin 37 and the receipt 52 include identical shapes, such as polygons including three or more sides, with the surface area of an attachment surface of the pin 37 being slightly smaller than an associated length and width that defines the receipt 52. As such, the pin 37 is received within the receipt 52 forming a press-fit within the receipt 52, such that the pin 37 is prevented from relative movement when disposed within the receipt 52. For example, in the embodiment shown in FIGS. 3E and 4A-4B, the pin 37 includes four sides and forms a square shape, and the receipt 52 is defined by a square shape that is designed to receive and retain the pin 37 therein.

In addition, the attachment mechanism between the cleaning disk 30 and the interior bottom surface 19 of the housing 12 includes a plurality of raised platforms 38 that extend in a direction away from the interior bottom surface 19 of the housing 12. In addition, the cleaning disk 30 includes a complementary plurality of raised platforms 39 that extend in a direction away from the bottom surface of the cleaning disk 30. The plurality of raised platforms 38, 39 of each of the interior bottom surface 19 of the housing 12 and the bottom surface of the cleaning disk 30 are circumferentially disposed about the central attachment point of each component. For example, in the embodiment in which the interior bottom surface 19 of the housing 12 includes a pin 37 extending in a direction away therefrom, and in which the cleaning disk 30 defines a central receipt 52, the plurality of raised platforms 38 on the interior bottom surface 19 of the housing 12 are circumferentially disposed about the pin 37, and the plurality of raised platforms 39 of the cleaning disk 30 are circumferentially disposed about the defined receipt 52. When the cleaning disk 30 mates with the interior bottom surface 19 of the housing 12 through the attachment mechanism of the pin-and-receipt, and discussed in detail above, the complementary raised platforms 38, 39 of each of the housing 12 and the cleaning disk 30 secure against each other to lock the cleaning disk 30 in place within the housing 12, thereby preventing the relative linear movement of the cleaning disk 30 with respect to the housing 12.

In use, each cleaning disk 30 rotates within the housing 12 upon actuation of each cleaning disk 30. As such, embodiments of the footwear cleaning system 10 include a set of gears that are in communication with each cleaning disk 30, either directly with the embodiment including the pin extending from the cleaning disk 30, or indirectly with the embodiment including the receipt 52 formed within the cleaning disk 30. The set of gears is designed to rotationally translate the pin 37, thereby rotating the cleaning disk 30 as a result. In an embodiment, the set of gears is disposed beneath the interior bottom surface 19 of the housing 12 and is in communication with a motor 44, such that once the motor 44 is actuated, the set of gears rotate.

Figure 4A:
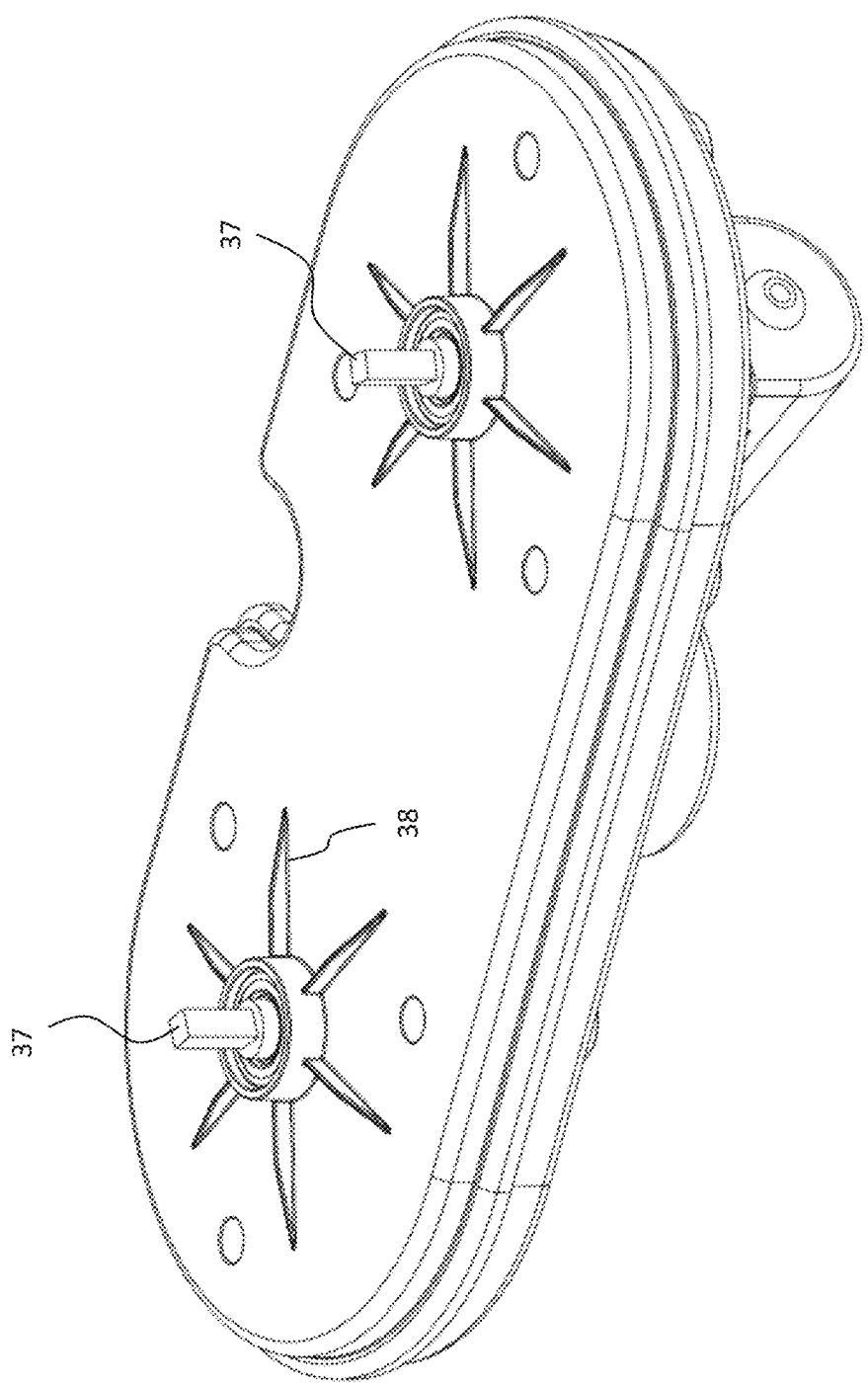
FIG. 4A is a perspective view of an attachment mechanism of a housing of a footwear cleaning system that is designed to receive and retain one or more cleaning disks thereto, in accordance with an embodiment of the present invention.

Referring to FIGS. 4A-4B, in an embodiment, a central gear 40 is in communication with the motor 44 via a drive shaft 49, with the central gear 40 being in direct communication with a second cleaning disk gear 42 and in indirect communication with a first cleaning disk gear 41 via an intermediary gear 43. As the central gear 40 rotates, the second cleaning disk gear 42 and the intermediary gear 43 rotate in opposing directions from the central gear 40 rotation, and the first cleaning disk gear 41 rotates in the same direction as the central gear 40 due to the intermediary gear 43. As such, the first cleaning disk gear 41 rotates in a counterclockwise direction, resulting in a first cleaning disk 30a within the housing 12 rotating in a counterclockwise direction. Similarly, the second cleaning disk gear 42 rotates in an opposite clockwise direction, resulting in a second cleaning disk 30b within the housing 12 rotating in a clockwise direction. As the first and second cleaning disks 30 within the housing 12 rotate in opposing directions, an item of footwear received within the housing 12 receives a rotational force that pulls the item of footwear toward the back end 14 of the housing 12 and away from the channel 20 that provides access to the internal compartment 18 of the housing 12. By exerting a pulling force on the item of footwear via the cleaning disks 30, the item of footwear is retained in place within the housing 12 without being ejected from the housing 12 in the absence of a positive external force, such as a force exerted by a user wearing the item of footwear. In an embodiment, the rotational speed of each cleaning disk 30 is between approximately 50-60 revolutions per minute to adequately clean the item of footwear.

In some embodiments, rather than including a set of gears, the footwear cleaning system 10 includes a rotational motor having a drive shaft that interfaces with a drive belt via a drive wheel. The drive belt further interfaces with pin that interacts with the cleaning disk 30 via a transition wheel. Thus, rotation of the drive shaft causes rotation of the cleaning disk 30. It should be appreciated that other embodiments may use any other assemblies configured to convert the output of the motor 44 into rotation of the cleaning disk 30.

Figure 5A:
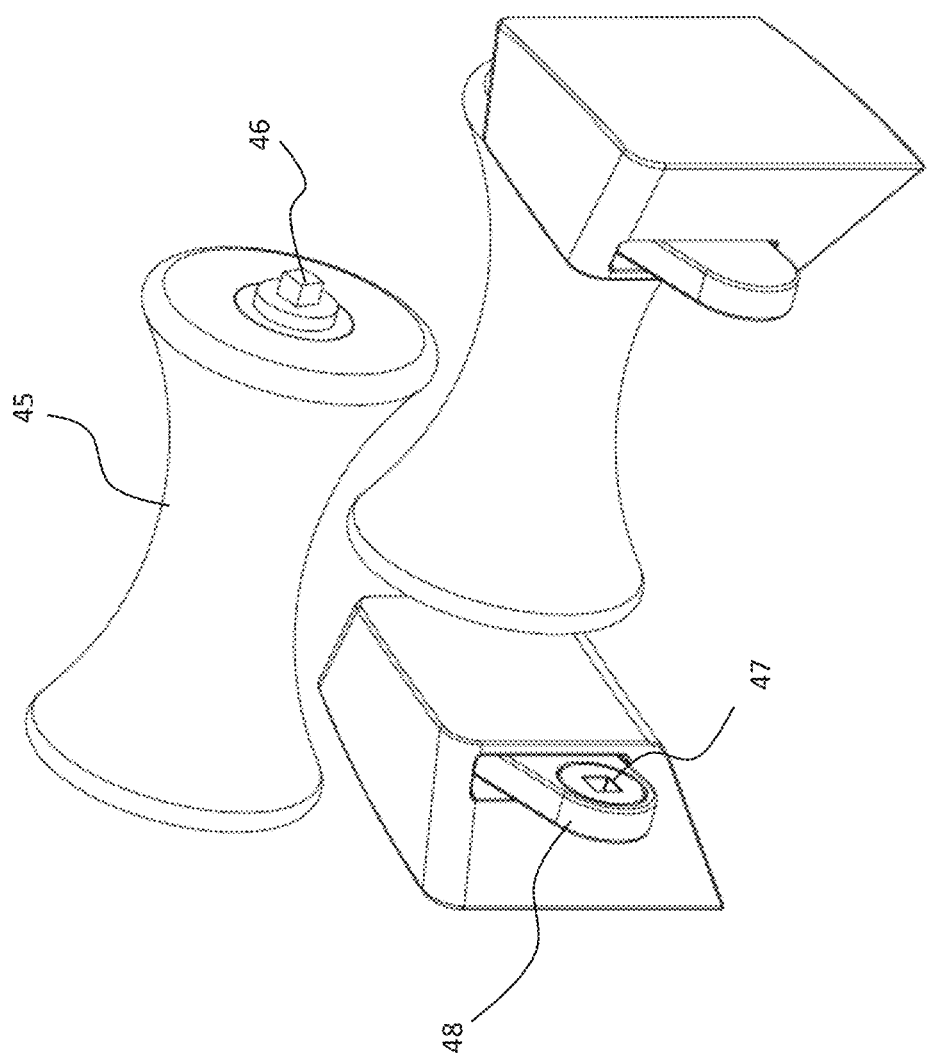
FIG. 5A is a perspective view of a buffer component of a footwear cleaning system, in accordance with an embodiment of the present invention.
Figure 5C:
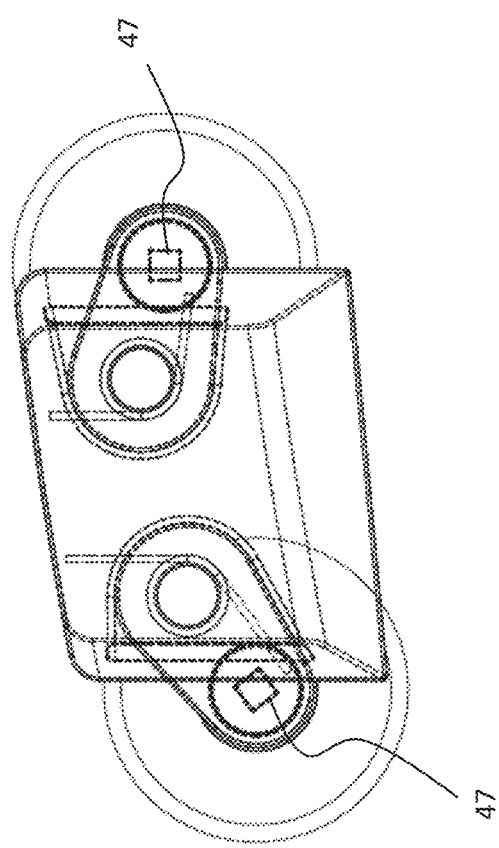
FIG. 5C is an internal orthogonal view of the buffer component and attachment point of FIG. 5B.

Referring now to FIGS. 5A-5C, in some embodiments, one or more buffers 45 are removably disposed proximate to the back end 14 of the internal compartment 18 of the housing 12, with each of the buffers 45 being spaced apart from the interior bottom surface 19 of the housing 12. As such, each buffer 45 is configured to contact one or more non-bottom surfaces of an item of footwear, such as a top surface, a side surface, a front surface (such as a toe-end surface of the footwear item), or other non-bottom surface of the item of footwear. As such, in an embodiment, each buffer 45 is shaped as a biconcave cylinder having a narrow body at a midpoint that extends to wider body portions at each end. The biconcave cylindrical shape of each buffer 45 is such that the buffer 45 includes a curved contacting surface that is capable of interacting with an item of footwear regardless of the shape of the item.

Each of the buffers 45 is designed to exert a force on the item of footwear to remove one or more contaminants therefrom, similar to the pads of the cleaning disk. To exert a force on the footwear item, each of the buffers 45 is connected to a motor that is disposed within the housing 12; in an embodiment, the motor to which the buffers are connected is the motor 44 to which the central gear 40 of the cleaning disk system is connected, such that an actuation of the motor 44 not only engages the central gear 40 of the cleaning disk system, but also rotates each of the buffers 45.

To removably secure each buffer 45 within the housing 12, a pair of opposing attachment points exist that are disposed proximate to opposing interior lateral surfaces 17 of the housing 12, such as being formed within or extending from one or more interior lateral surfaces 17 defining the internal compartment 18 of the housing 12. Similar to the attachment mechanism for the cleaning disk 30 and the interior bottom surface 19 of the housing 12, an embodiment of the buffer attachment mechanism includes a receipt 47 that is defined within an arm 48 disposed proximate to an interior lateral surface 17 of the housing 12, with an extension 46 projecting from a side surface of the buffer 45. As such, the extension 46 projecting from the buffer 45 is receivable within the receipt 47 defined within the arm 48 of the housing 12, thereby securing the buffer 45 within the housing 12. It should be appreciated that an opposite mechanism, wherein the buffer 45 includes a side surface that defines a receipt therein, and wherein the attachment mechanism within the housing 12 includes an extension projecting therefrom, is contemplated in some embodiments. Moreover, it should be appreciated that each buffer 45 is selectively removable and replaceable from the housing 12, such as if the buffer 45 deteriorates due to frictional forces between the buffer 45 and the item of footwear. To decrease a likelihood of deterioration of the buffer 45, embodiments of the buffer 45 are made of a material such as an open cell foam material, a closed cell foam material, a sponge material, and/or a brush-like materials, such that the buffer 45 is capable of scrubbing the item of footwear without deteriorating due to frictional forces.

To accommodate for the cleaning of both a toe end of an item of footwear, as well as a top surface of the item, an embodiment of the system 10 includes a first buffer 45a spaced apart from a second buffer 45b. The first buffer 45a is disposed proximate to the back end 14 of the housing 12, such that the first buffer 45a is configured to contact the toe end of the footwear item. The second buffer 45b is disposed between the first buffer 45a and the front end 13 of the housing 12, such that the second buffer 45b is configured to contact the top surface of the footwear item. Since the toe end of a footwear item typically resides at a vertical point in space that is between the bottom surface of the footwear item and the top surface of the footwear item (such as the laces of a shoe), the second buffer 45b is disposed at a height as defined by a distance from the interior bottom surface 19 of the housing 12 that is greater than an associated height of the first buffer 45a. As such, along a vertical axis, the first buffer 45a is disposed between the interior bottom surface 19 of the housing 12 and the second buffer 45b, such that both the toe end of the footwear item and the top surface of the item can be cleaned of contaminants by each buffer 45.

In some embodiments, the relative position of at least one buffer 45 is adjustable to accommodate for footwear items of varying shapes, sizes, and dimensions, thereby providing a universal buffer system. As such, the buffer mechanism includes a pair or pivotable arms 48 that are each disposed on opposing sides of the housing 12, such that at least one of the buffers 45 can be adjusted through an arcing movement of each pivotable arm 48 which raises and lowers the height of the associated buffer 45. It should be appreciated that each buffer 45 can be adjusted through a similar opposing arm adjustment mechanism. Moreover, it should be appreciated that a pair of singular arms 48 can be disposed on opposing sides of the housing 12, such that an adjustment of a height of one buffer 45 consequently adjusts a height of another buffer 45. For example, raising a height of the second buffer 45b consequently lowers a height of the first buffer 45a, and raising a height of the first buffer 45a consequently lowers a height of the second buffer 45b.

In addition, in some embodiments, the interior bottom surface 19 of the housing 12 includes a transparent section 55 proximate to the back end 14 of the housing 12, approximately beneath the one or more buffers 45 (shown in particular in FIG. 2C). The transparent section 55 of the interior bottom surface 19 resides above one or more ultraviolet (UV) light sources 46 that are secured within the housing 12 and oriented such that light emitted from the UV light source(s) 46 is directed toward the internal compartment 18 of the housing 12. As such, the UV light source(s) 46 are configured to subject the footwear item to UV radiation, further removing contaminants from the item of footwear.

Figure 6A:
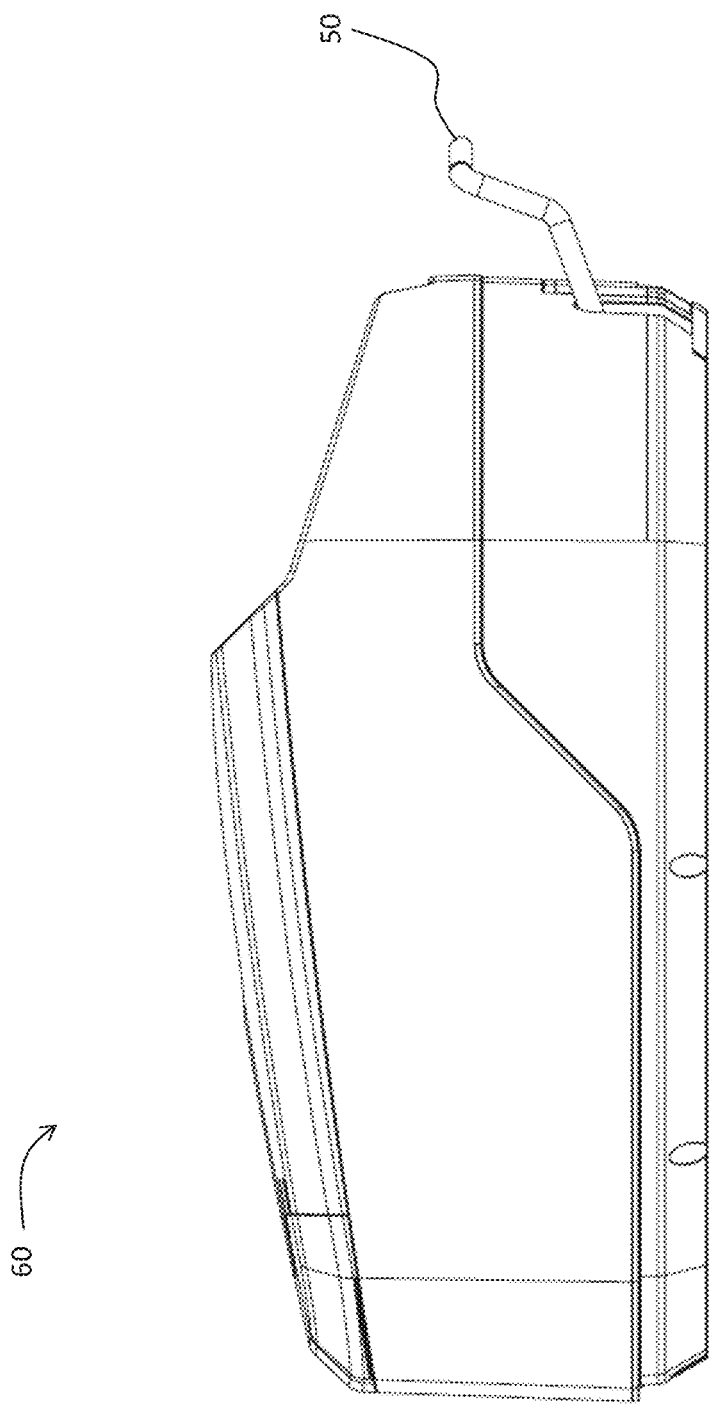
FIG. 6A is an orthogonal view of a footwear cleaning system showing an actuating lever in a default configuration, in which the footwear cleaning system is not in use, in accordance with an embodiment of the present invention.

Referring now to FIGS. 6A-6B, as noted above, an actuation mechanism is used to engage one or more motors and pumps within embodiments of the footwear cleaning system 10, thereby beginning a cleaning cycle within the system 10. In an embodiment of the system 10, the actuation mechanism is a lever 50 that is disposed at the front end 13 of the housing 12, extending in a direction away from the housing 12 and configured to be disposed between a user and the housing 12. The cleaning system 10 is actuated when the lever 50 contacts a pressure switch that is disposed beneath the lever 50 in the absence of receiving a downward force. As such, the lever 50 at the front end 13 of the housing 12 is configured to receive a force from a user to engage the motor 44 and transmit instructions via an internal control box to clean an item of footwear that is disposed within the housing 12.

For example, in an embodiment, a user places one foot that is disposed within an item of footwear within the housing 12 via the channel 20 disposed at the front end 13 of the housing 12. The user then exerts a downward force on the lever 50 (such as by an opposite foot), thereby translating the lever 50 from a default configuration 60 (i.e., an "off" mode) to an in-use configuration 70 (i.e., an "on" mode), with the translation of the lever 50 engaging the motor 44. The motor and the control box then engage the central gear 40 to rotate the one or more cleaning disks 30, rotate the buffer(s) 45, turn on the UV light source(s) 56, and transmit instructions to one or more fluid reservoirs 25 to pump a fluid disposed therein to one or more dispensing nozzles 26. In embodiments, each function of the footwear cleaning system 10 engages for a predetermined period of time, forming a comprehensive cleaning system 10 once engaged by the actuation mechanism and terminating after the predetermined period of time expires. While a lever 50 and pressure sensor system is described above, it should be appreciated that the motor can be engaged by alternative methods and/or devices known to a person of ordinary skill in the art, including but not limited to remote controllers, manual switches, and motion sensors.

To accomplish cleaning within a predetermined amount of time, embodiments of the system 10 include timing circuitry to control the relative and/or individual timing of the motor 44 and fluid pump(s) that are in communication with the fluid reservoir(s) 25. Some embodiments include timing circuitry that automatically shuts off the motor 44 and/or fluid pump(s) after a predetermined amount of time lapses from when the lever 50 receives a downward force, such as from a user.

The advantages set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention that, as a matter of language, might be said to fall therebetween.

What is claimed is:

1. A footwear cleaning disk configured for use in combination with a footwear cleaning system including a housing, the footwear cleaning disk comprising:
   a body including a top surface opposite a bottom surface with a central receipt defined within the body;
   wherein the body includes a top section terminating at the top surface and a bottom section terminating at the bottom surface, the top section and the bottom section being selectively decouplable from each other;
   a first section of the body including a plurality of bristles extending in a direction away from the top surface of the body, such that the plurality of bristles terminate at a first height with respect to the top surface of the body; and
   a second section of the body disposed adjacent to the first section of the body, the second section of the body including a pad having a planar top contact surface disposed at a second height with respect to the top surface of the body, the second height being less than the first height, wherein the central receipt defined within the body of the cleaning disk is configured to receive a complementary attachment point of the housing of the footwear cleaning system, wherein an item of footwear is configured to reside adjacent to the top surface of the body of the cleaning disk, and wherein the plurality of bristles and the planar top contact surface of the pad are configured to synergistically remove contaminants from the item of footwear by the plurality of bristles loosening contaminants from a bottom surface of the item of footwear, and by the top contact surface of the pad translating the loosened contaminants in a direction away from the item of footwear.

2. The footwear cleaning disk of claim 1, further comprising a plurality of alternating sections of flexible bristles and pads, such that the second section of the body including the pad is disposed adjacent to a third section of the body including a plurality of bristles, and such that the third section of the body including the plurality of bristles is disposed adjacent to a fourth section of the body including a pad.

3. The footwear cleaning disk of claim 2, further comprising a fifth section of the body including a plurality of bristles, the fifth section of the body being disposed adjacent to the fourth section of the body including the pad.

4. The footwear cleaning disk of claim 3, further comprising a sixth section of the body including a pad, the sixth section of the body being disposed between the fifth section of the body including the plurality of bristles and the first section of the body including the plurality of bristles.

5. The footwear cleaning disk of claim 1, wherein the plurality of bristles include a cumulative surface area that occupies approximately half of a surface area of the top surface of the body.

6. The footwear cleaning disk of claim 1, wherein the pad includes a cumulative surface area that occupies approximately half of a surface area of the top surface of the body.

7. The footwear cleaning disk of claim 1, wherein the first section of the body is made of a flexible material having a hardness of between approximately 25 and 40 Shore A.

8. The footwear cleaning disk of claim 1, wherein the second section of the body is made of an open cell foam material selected from the group consisting of reticulated polyurethane foam, urethane foam, polyethylene foam, neoprene foam, silicone foam, and combinations thereof.

9. The footwear cleaning disk of claim 1, further comprising at least one tab extending radially from a lateral side wall of the top section of the body.

10. The footwear cleaning disk of claim 9, further comprising at least one complementary receipt formed within a lateral side wall of the bottom section of the body, the at least one complementary receipt configured to receive and retain the at least one tab.

11. The footwear cleaning disk of claim 1, further comprising an indentation formed within the body, the indentation defined by opposing lateral side walls joined together by a longitudinal bottom wall that is disposed between the top surface and the bottom surface of the body.

12. The footwear cleaning disk of claim 11, wherein the pad is disposed within the indentation, such that the opposing lateral side walls are configured to prevent a linear translation of the pad during contact with the item of footwear.

13. The footwear cleaning disk of claim 1, further comprising a plurality of raised platforms extending from the bottom surface of the body, the plurality of raised platforms extending in a direction away from the top surface of the body, wherein the plurality of raised platforms are configured to secure against a complementary attachment point within the housing of the footwear cleaning system.

14. A footwear cleaning system comprising:
a housing having a front end opposite a rear end, the housing including one or more discontinuous external walls and an interior bottom surface, the one or more discontinuous external walls defining a channel within the front end of the housing, the one or more discontinuous external walls and the interior bottom surface defining an internal compartment formed therebetween, with the channel providing access to the internal compartment;
a pin extending in a direction away from the interior bottom surface of the housing and terminating at a point within the internal compartment of the housing; and
a cleaning disk secured to the pin, the cleaning disk including:
a body including a top surface opposite a bottom surface with a central receipt defined within the body;
a first section of the body including a plurality of bristles extending in a direction away from the top surface of the body, such that the plurality of bristles terminate at a first height with respect to the top surface of the body; and
a second section of the body disposed adjacent to the first section of the body, the second section of the body including a pad having a planar top contact surface disposed at a second height with respect to the top surface of the body, the second height being less than the first height,
wherein the central receipt defined within the body of the cleaning disk is configured to receive the pin therein,
wherein the internal compartment is configured to receive an item of footwear via the channel,
wherein the item of footwear is configured to reside adjacent to the top surface of the body of the cleaning disk, and
wherein the plurality of bristles and the planar top contact surface of the pad are configured to synergistically remove contaminants from the item of footwear by the plurality of bristles loosening contaminants from a bottom surface of the item of footwear, and by the top contact surface of the pad translating the loosened contaminants in a direction away from the item of footwear.

15. The footwear cleaning system of claim 14, wherein the cleaning disk further comprises a plurality of alternating sections of flexible bristles and pads, such that the second section of the body including the pad is disposed adjacent to a third section of the body including a plurality of bristles, and such that the third section of the body including the plurality of bristles is disposed adjacent to a fourth section of the body including a pad.

16. The footwear cleaning system of claim 14, wherein the cleaning disk further comprises an indentation formed within the body, the indentation defined by opposing lateral side walls joined together by a longitudinal bottom wall that is disposed between the top surface and the bottom surface of the body.

17. The footwear cleaning system of claim 16, wherein the pad is disposed within the indentation, such that the opposing lateral side walls are configured to prevent a linear translation of the pad during contact with the item of footwear.

18. The footwear cleaning system of claim 14, further comprising a plurality of raised housing platforms extending in a direction away from the interior bottom surface of the housing.

19. The footwear cleaning system of claim 18, further comprising a plurality of raised cleaning disk platforms extending from the bottom surface of the body of the cleaning disk, the plurality of raised cleaning disk platforms extending in a direction away from the top surface of the body, wherein the plurality of raised cleaning disk platforms are configured to secure against the plurality of raised housing platforms to secure the cleaning disk within the housing.

\* \* \* \* \*